(12) United States Patent
Nalagatla et al.

(10) Patent No.: US 11,051,809 B2
(45) Date of Patent: Jul. 6, 2021

(54) CARTRIDGE RECEIVING JAW FOR SURGICAL STAPLER AND ASSOCIATED METHOD OF MANUFACTURE WITH MIM

(71) Applicant: ETHICON LLC, Guaynabo, PR (US)

(72) Inventors: Anil K. Nalagatla, Mason, OH (US); Frederick E. Shelton, IV, Hillsboro, OH (US); Chester O. Baxter, III, Loveland, OH (US); Gregory J. Bakos, Mason, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 1 day.

(21) Appl. No.: 16/236,714

(22) Filed: Dec. 31, 2018

(65) Prior Publication Data

US 2020/0205816 A1     Jul. 2, 2020

(51) Int. Cl.
| | |
|---|---|
| *A61B 17/072* | (2006.01) |
| *B21K 5/00* | (2006.01) |
| *B23K 9/02* | (2006.01) |
| *B33Y 10/00* | (2015.01) |

(52) U.S. Cl.
CPC .............. *A61B 17/072* (2013.01); *B21K 5/00* (2013.01); *B23K 9/02* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *B33Y 10/00* (2014.12)

(58) Field of Classification Search
CPC ........... A61B 17/072; B21K 5/00; B23K 9/02
See application file for complete search history.

(56) References Cited

U.S. PATENT DOCUMENTS

| | | |
|---|---|---|
| 5,163,945 A | 11/1992 | Ortiz et al. |
| 5,205,459 A | 4/1993 | Brinkerhoff et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |

(Continued)

FOREIGN PATENT DOCUMENTS

| | | |
|---|---|---|
| EP | 3 106 101 A1 | 12/2016 |
| EP | 3 613 358 A1 | 2/2020 |

OTHER PUBLICATIONS

European Search Report, Partial, and Provisional Written Opinion dated Mar. 25, 2020 for Application No. EP 19220047.5, 17 pgs.

(Continued)

*Primary Examiner* — Nathaniel C Chukwurah
(74) *Attorney, Agent, or Firm* — Frost Brown Todd LLC

(57) ABSTRACT

A method is used to manufacture an end effector of a surgical instrument. The end effector includes first and second opposing jaws. The first jaw includes a body and an elongate cap. The method includes providing the elongate cap and the body of the first jaw of the end effector. The body includes an elongate channel and at least one alignment feature. The method also includes aligning the elongate cap with the elongate channel that extends completely through the body using the at least one alignment feature of the body that is disposed adjacent the elongate channel. The method also includes welding the elongate cap onto the body to at least partially enclose the elongate channel.

17 Claims, 18 Drawing Sheets

(56) References Cited

U.S. PATENT DOCUMENTS

| | | |
|---|---|---|
| 5,333,773 A | 8/1994 | Main et al. |
| 5,342,373 A | 8/1994 | Stefanchik et al. |
| 5,350,104 A | 9/1994 | Main et al. |
| 5,403,312 A | 4/1995 | Yates et al. |
| 5,431,668 A | 7/1995 | Burbank, III et al. |
| 5,445,167 A | 8/1995 | Yoon et al. |
| 5,533,661 A | 7/1996 | Main et al. |
| 5,601,573 A | 2/1997 | Fogelberg et al. |
| 5,951,574 A | 9/1999 | Stefanchik et al. |
| 6,988,650 B2 | 1/2006 | Schwemberger et al. |
| 7,000,818 B2 * | 2/2006 | Shelton, IV ..... A61B 17/07207 227/176.1 |
| 7,134,587 B2 | 11/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,261,724 B2 | 8/2007 | Molitor et al. |
| 7,380,696 B2 | 6/2008 | Shelton, IV et al. |
| 7,422,139 B2 | 9/2008 | Shelton, IV et al. |
| 7,464,849 B2 | 12/2008 | Shelton, IV et al. |
| 7,670,334 B2 | 3/2010 | Hueil et al. |
| 7,686,820 B2 | 3/2010 | Huitema et al. |
| 7,699,860 B2 | 4/2010 | Huitema et al. |
| 7,731,724 B2 | 6/2010 | Huitema et al. |
| 7,753,245 B2 | 7/2010 | Boudreaux et al. |
| 7,845,537 B2 | 12/2010 | Shelton, IV et al. |
| 7,980,443 B2 | 7/2011 | Scheib et al. |
| 8,038,686 B2 | 10/2011 | Huitema et al. |
| 8,210,411 B2 | 7/2012 | Yates et al. |
| 8,220,688 B2 | 7/2012 | Laurent et al. |
| 8,262,679 B2 | 9/2012 | Nguyen |
| 8,308,040 B2 | 11/2012 | Huang et al. |
| 8,393,514 B2 | 3/2013 | Shelton, IV et al. |
| 8,408,439 B2 | 4/2013 | Huang et al. |
| 8,453,914 B2 | 6/2013 | Laurent et al. |
| 8,561,870 B2 | 10/2013 | Baxter, III et al. |
| 8,608,045 B2 | 12/2013 | Smith et al. |
| 8,733,613 B2 | 5/2014 | Huitema et al. |
| 8,910,847 B2 | 12/2014 | Nalagatla et al. |
| 9,072,535 B2 | 7/2015 | Shelton, IV et al. |
| 9,101,358 B2 | 8/2015 | Kerr et al. |
| 9,186,142 B2 | 11/2015 | Fanelli et al. |
| 9,345,481 B2 | 5/2016 | Hall et al. |
| 9,517,065 B2 | 12/2016 | Simms et al. |
| 9,713,469 B2 | 7/2017 | Leimbach et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 9,867,615 B2 | 1/2018 | Fanelli et al. |
| 9,907,552 B2 | 3/2018 | Measamer et al. |
| 9,936,949 B2 | 4/2018 | Measamer et al. |
| 10,092,292 B2 | 10/2018 | Boudreaux et al. |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2006/0212069 A1 * | 9/2006 | Shelton, IV ......... A61B 17/072 606/205 |
| 2007/0175955 A1 | 8/2007 | Shelton, IV et al. |
| 2014/0239037 A1 | 8/2014 | Boudreaux et al. |
| 2014/0263552 A1 | 9/2014 | Hall et al. |
| 2015/0083772 A1 | 3/2015 | Miller et al. |
| 2015/0083773 A1 | 3/2015 | Measamer et al. |
| 2015/0083774 A1 | 3/2015 | Measamer et al. |
| 2015/0083775 A1 | 3/2015 | Leimbach et al. |
| 2016/0374672 A1 | 12/2016 | Bear et al. |
| 2017/0008117 A1 * | 1/2017 | Siefert ................. B23K 33/004 |
| 2017/0027571 A1 | 2/2017 | Nalagatla et al. |
| 2017/0258471 A1 | 9/2017 | DiNardo et al. |
| 2018/0132849 A1 | 5/2018 | Miller et al. |
| 2018/0132853 A1 | 5/2018 | Miller et al. |
| 2018/0168620 A1 * | 6/2018 | Huang ............. A61B 17/07207 |
| 2018/0168647 A1 | 6/2018 | Shelton, IV et al. |
| 2018/0310938 A1 | 11/2018 | Kluener et al. |
| 2018/0310939 A1 | 11/2018 | Stager et al. |
| 2018/0325502 A1 | 11/2018 | Swader et al. |
| 2018/0368841 A1 | 12/2018 | Shelton, IV et al. |

OTHER PUBLICATIONS

European Search Report, Extended, and Written Opinion dated Jul. 10, 2020 for Application No. EP 1920047.5, 17 pgs.

International Search Report and Written Opinion dated Jun. 23, 2020 for Application No. PCT/IB2019/061246, 21 pgs.

* cited by examiner

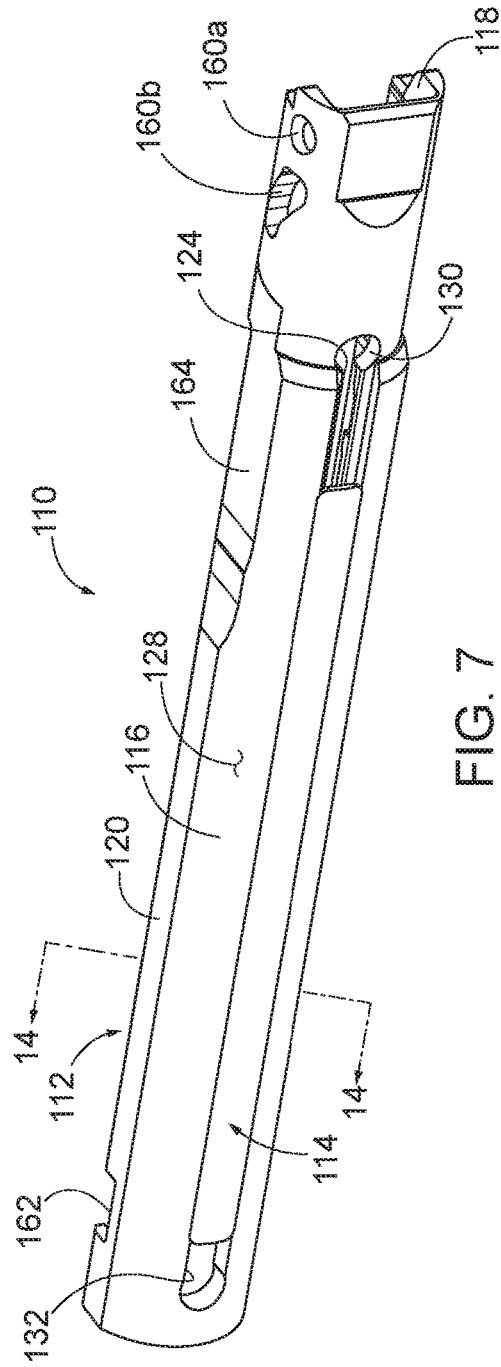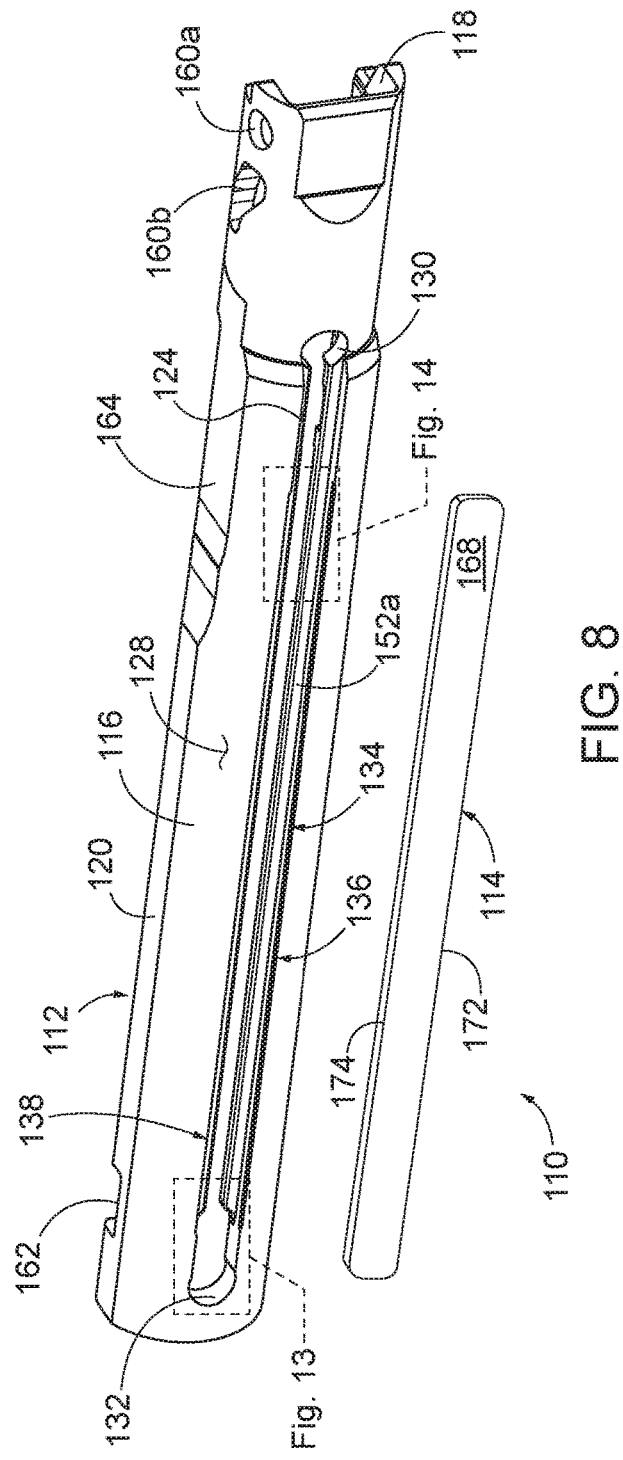

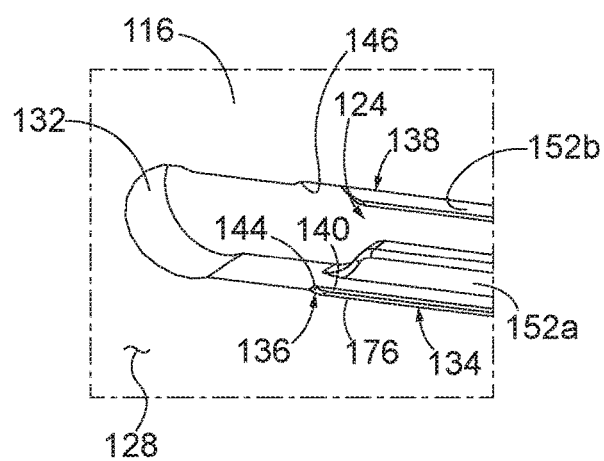
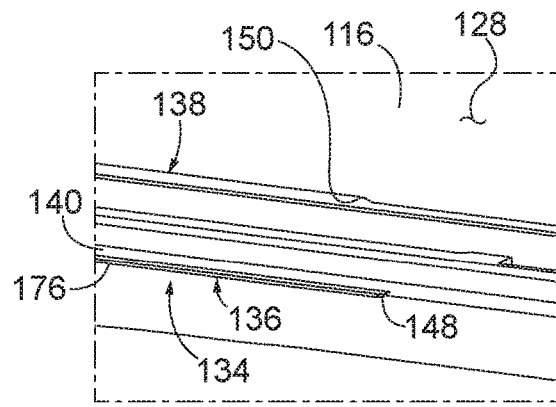
FIG. 12  FIG. 13
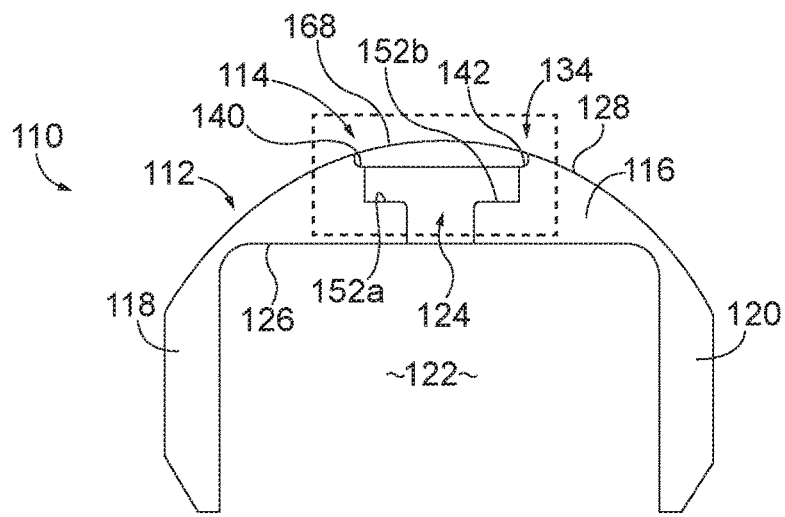
FIG. 14
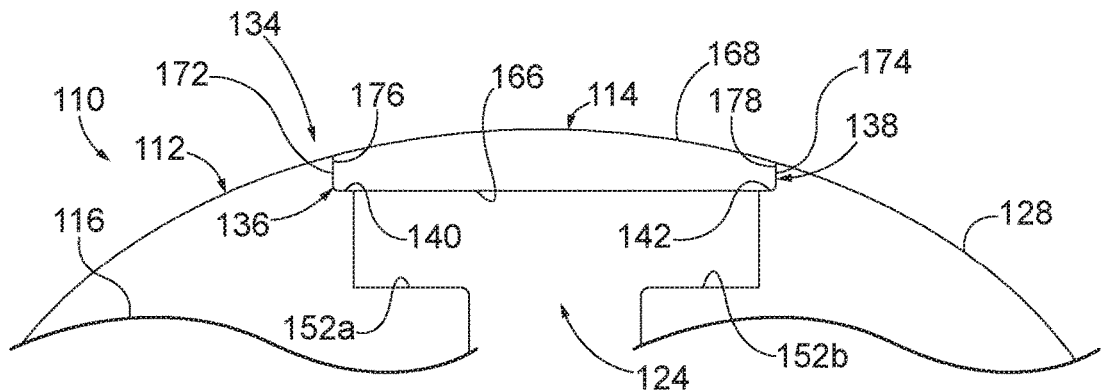
FIG. 14A

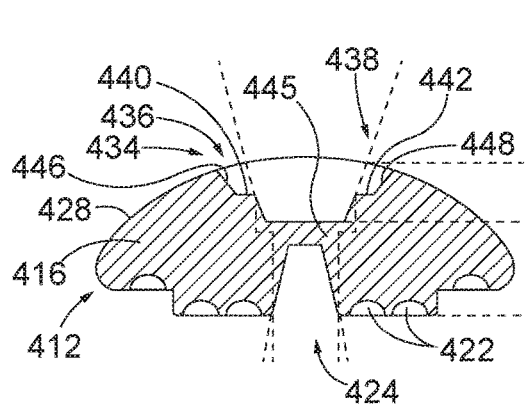 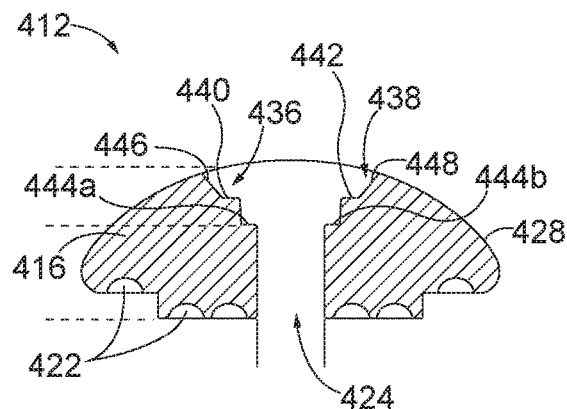
FIG. 23A　　　　FIG. 23B
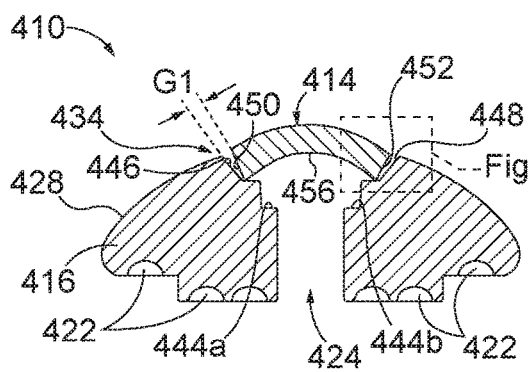 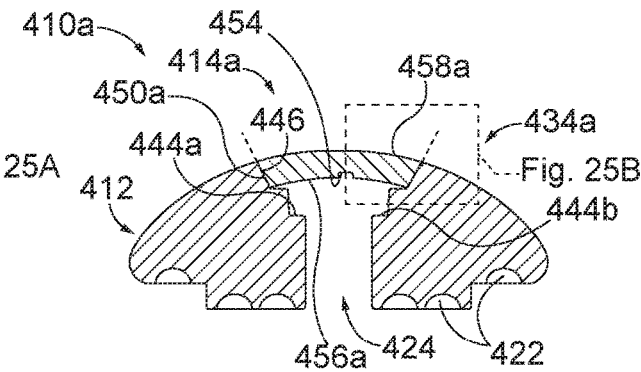
FIG. 24A　　　　FIG. 24B
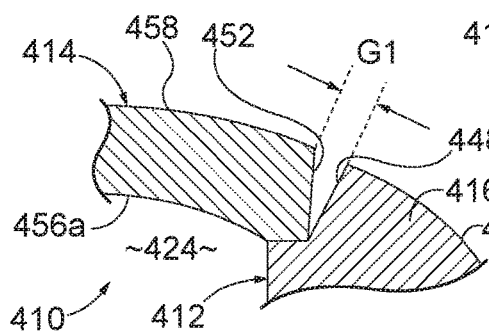 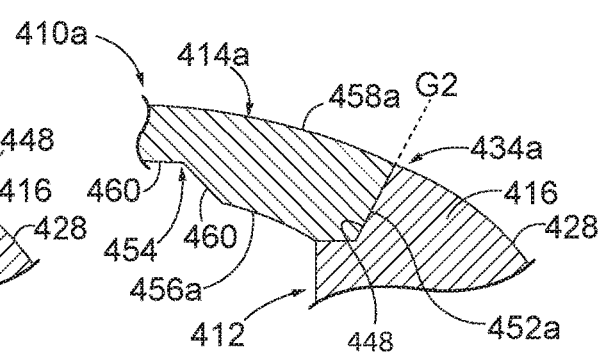
FIG. 25A　　　　FIG. 25B

CARTRIDGE RECEIVING JAW FOR SURGICAL STAPLER AND ASSOCIATED METHOD OF MANUFACTURE WITH MIM

BACKGROUND

Endoscopic surgical instruments may include a shaft between the end effector and a handle portion, which is manipulated by the clinician. Such a shaft may enable insertion through a trocar to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 7 depicts a bottom right perspective view of a first exemplary alternative lower jaw that may be incorporated into the instrument of FIG. 1;

FIG. 8 depicts an exploded bottom right perspective view of the lower jaw of FIG. 7 with the lower jaw body and the elongate cap separated;

FIG. 12 depicts an enlarged perspective view of distal alignment features of the lower jaw body of FIG. 8;

FIG. 13 depicts an enlarged perspective view of proximal alignment features of the lower jaw body of FIG. 8;

FIG. 14 depicts a cross-sectional view of the lower jaw and the elongate cap of FIG. 7, taken along line 14-14 of FIG. 7;

FIG. 14A depicts an enlarged cross-sectional view of the lower jaw body and the elongate cap of FIG. 14;

FIG. 23A depicts a schematic sectional view of the anvil body of FIG. 20 after being formed but prior to being machined;

FIG. 23B depicts a schematic sectional view of the anvil body of FIG. 23A after being machined;

FIG. 24A depicts a schematic sectional view of the anvil body of FIG. 23B and the elongate cap of FIG. 19;

FIG. 24B depicts a schematic sectional view of the anvil of FIG. 23B and an exemplary elongate cap;

FIG. 25A depicts a schematic sectional view of an enlarged portion of a lateral gap between the anvil body and the elongate cap of FIG. 24A;

FIG. 25B depicts a schematic sectional view of an enlarged portion of the fit between the anvil body and the elongate cap of FIG. 24B;

Figure 1:
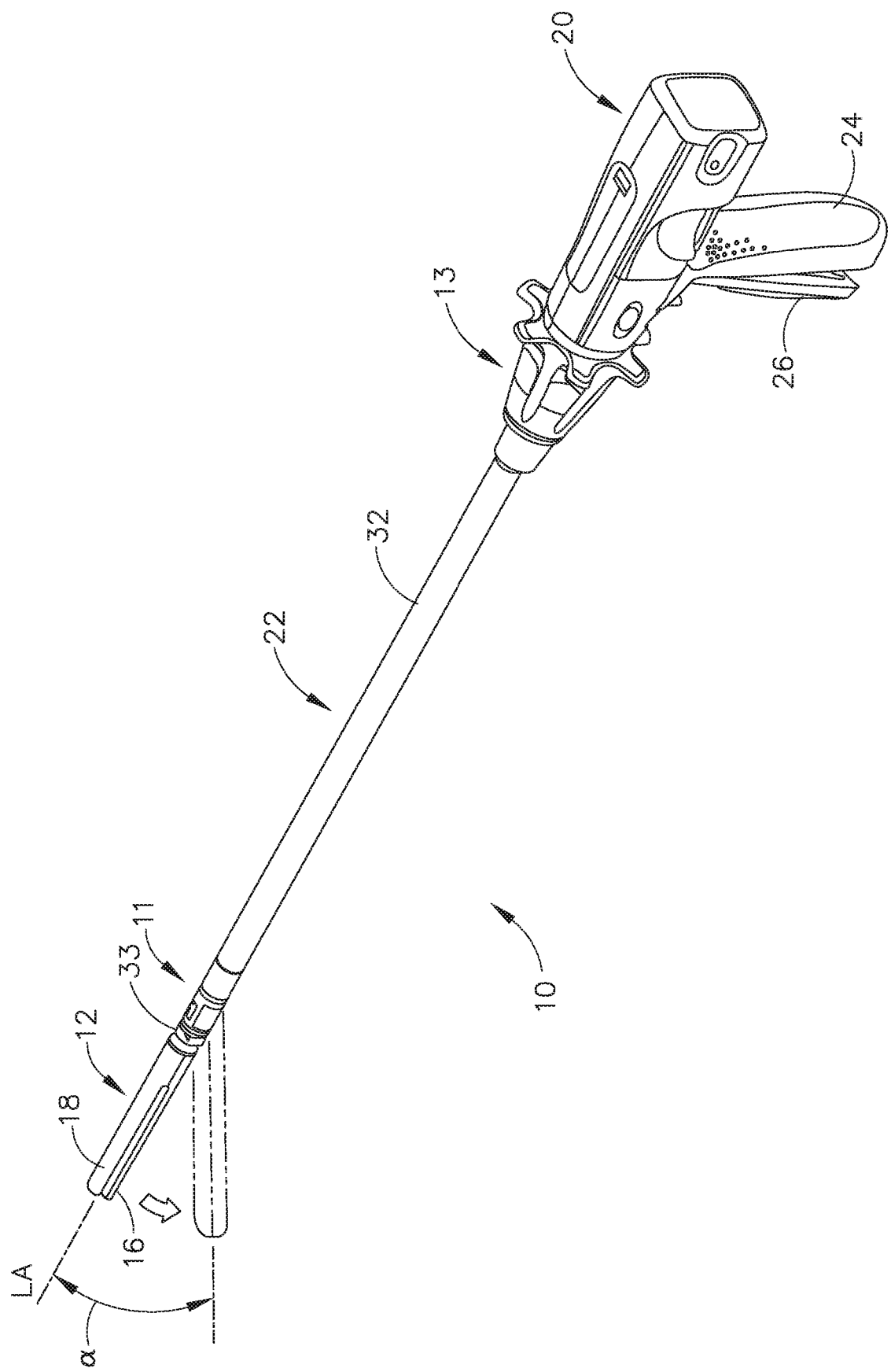
FIG. 1 depicts a perspective view of a first exemplary surgical stapling instrument.
Figure 2:
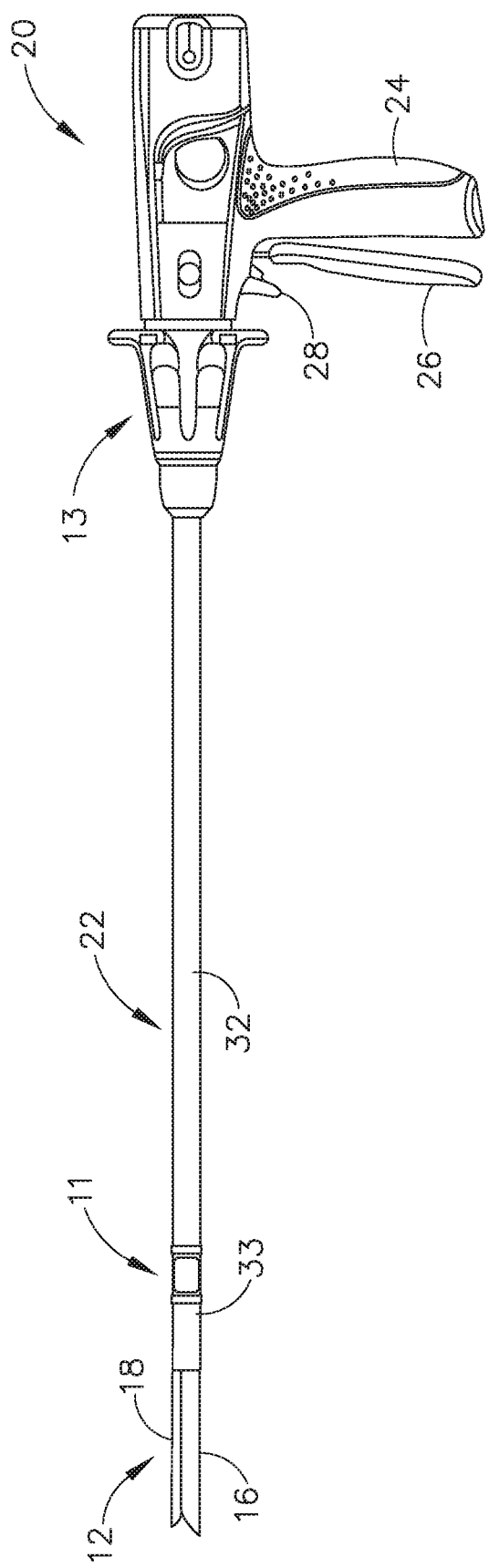
FIG. 2 depicts a side view of the instrument of FIG. 1 with a first exemplary end effector.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers to the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. First Exemplary Surgical Instrument Having a First Exemplary End Effector

FIGS. 1-6 depict a first exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a body, (shown as a handle portion (20)), connected to a shaft (22), which distally terminates in an articulation joint (11), which is further coupled with a first exemplary end effector (12). Shaft (22) may be constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). Articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein; and/or U.S. Pat. No. 9,795,379, the disclosure of which is incorporated by reference herein.

End effector (12) of the present example includes a lower jaw (16) and a pivotable anvil (18). Lower jaw (16) may be constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33). Handle portion (20) also includes a firing trigger (28) (shown in FIG. 2). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

FIGS. 3-6 depict end effector (12) employing an E-beam form of firing beam (14). As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within an elongate channel (42) of anvil (18). Firing beam cap (44) slidably engages a lower surface of lower jaw (16) by having firing beam (14) extend through an elongate channel (45) (shown in FIG. 4B) that is formed through lower jaw (16). Middle pin (46) slidingly engages a top surface of lower jaw (16), cooperating with firing beam cap (44). Firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein.

Figure 3:
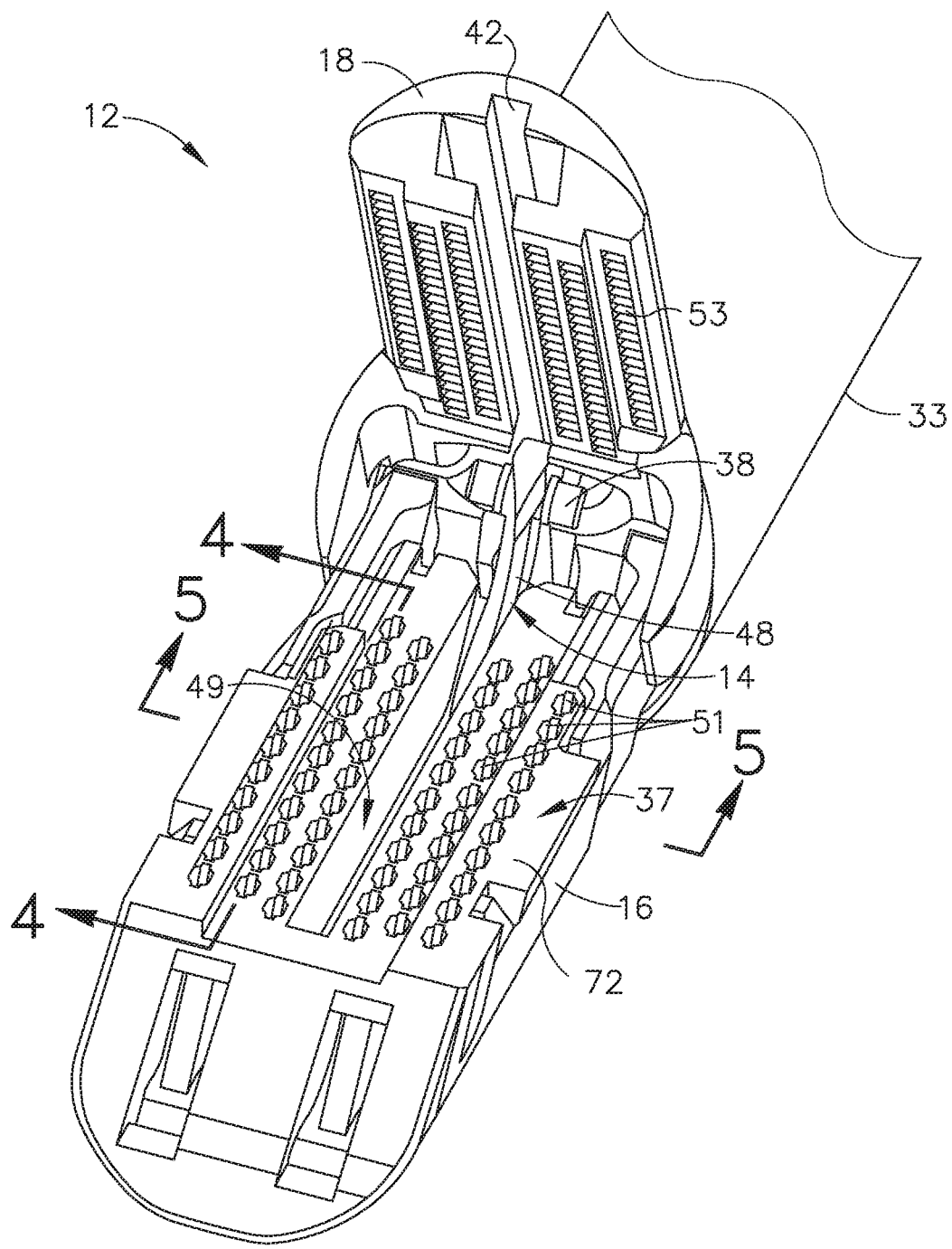
FIG. 3 depicts a perspective view of the end effector of the instrument of FIG. 1 in an open configuration.
Figure 4A:
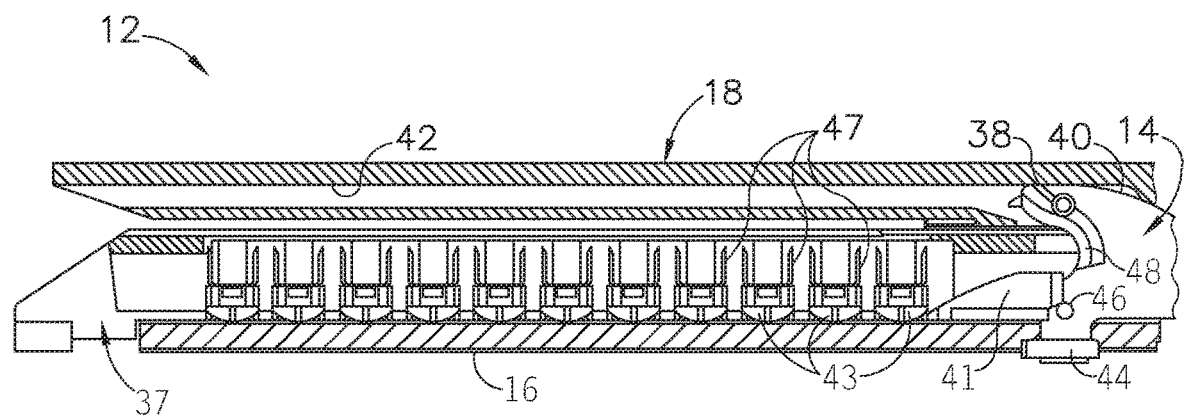
FIG. 4A depicts a side cross-sectional view of the end effector of FIG. 3, taken along line 4-4 of FIG. 3, with the firing beam in a proximal position.
Figure 4B:
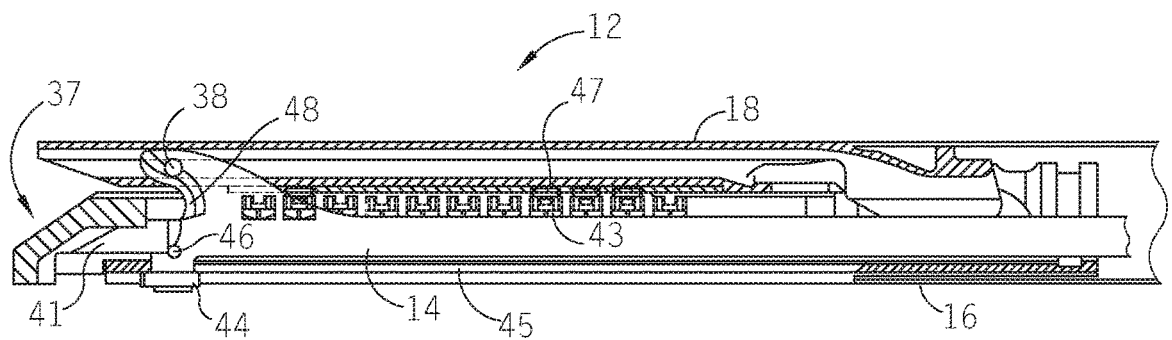
FIG. 4B depicts a side cross-sectional view of the end effector of FIG. 3, taken along line 4-4 of FIG. 3, with the firing beam in a distal position.
Figure 5:
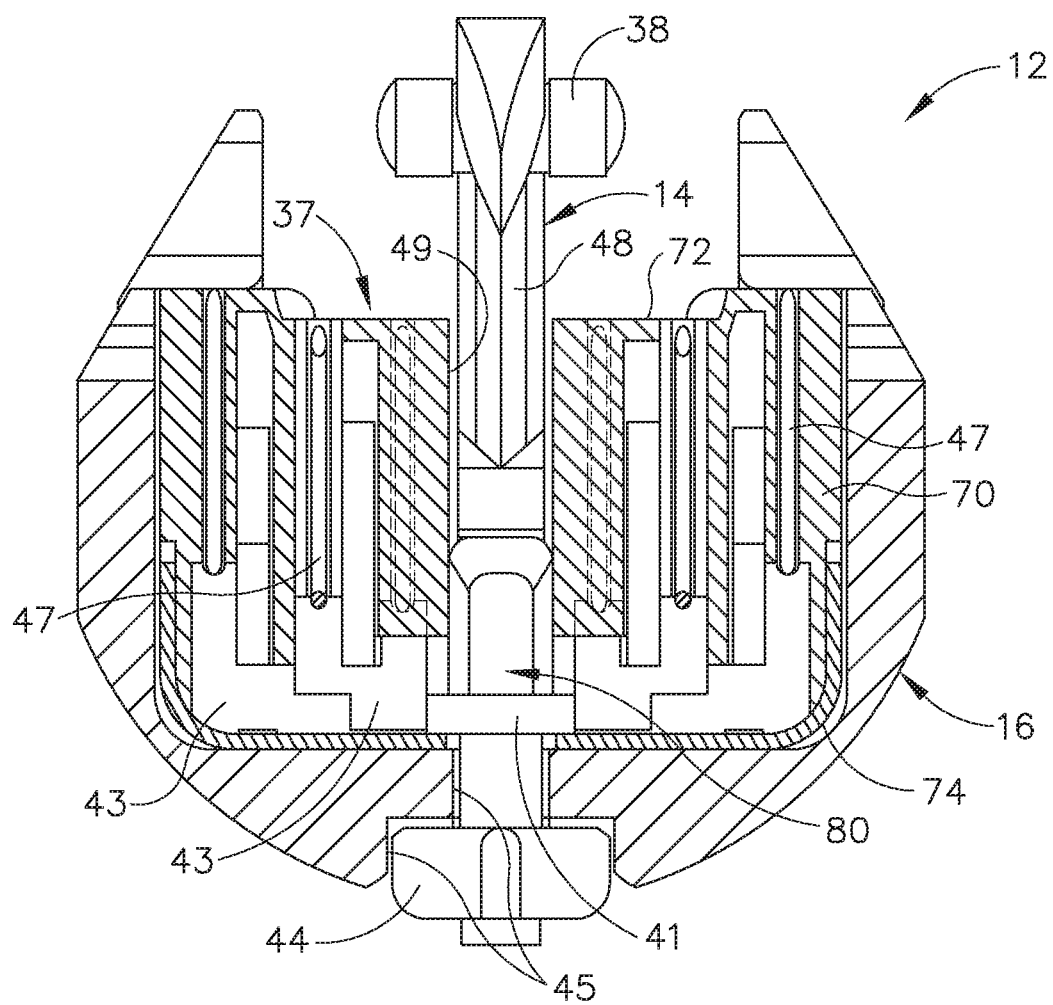
FIG. 5 depicts an end cross-sectional view of the end effector of FIG. 3, taken along line 5-5 of FIG. 3.
Figure 6:
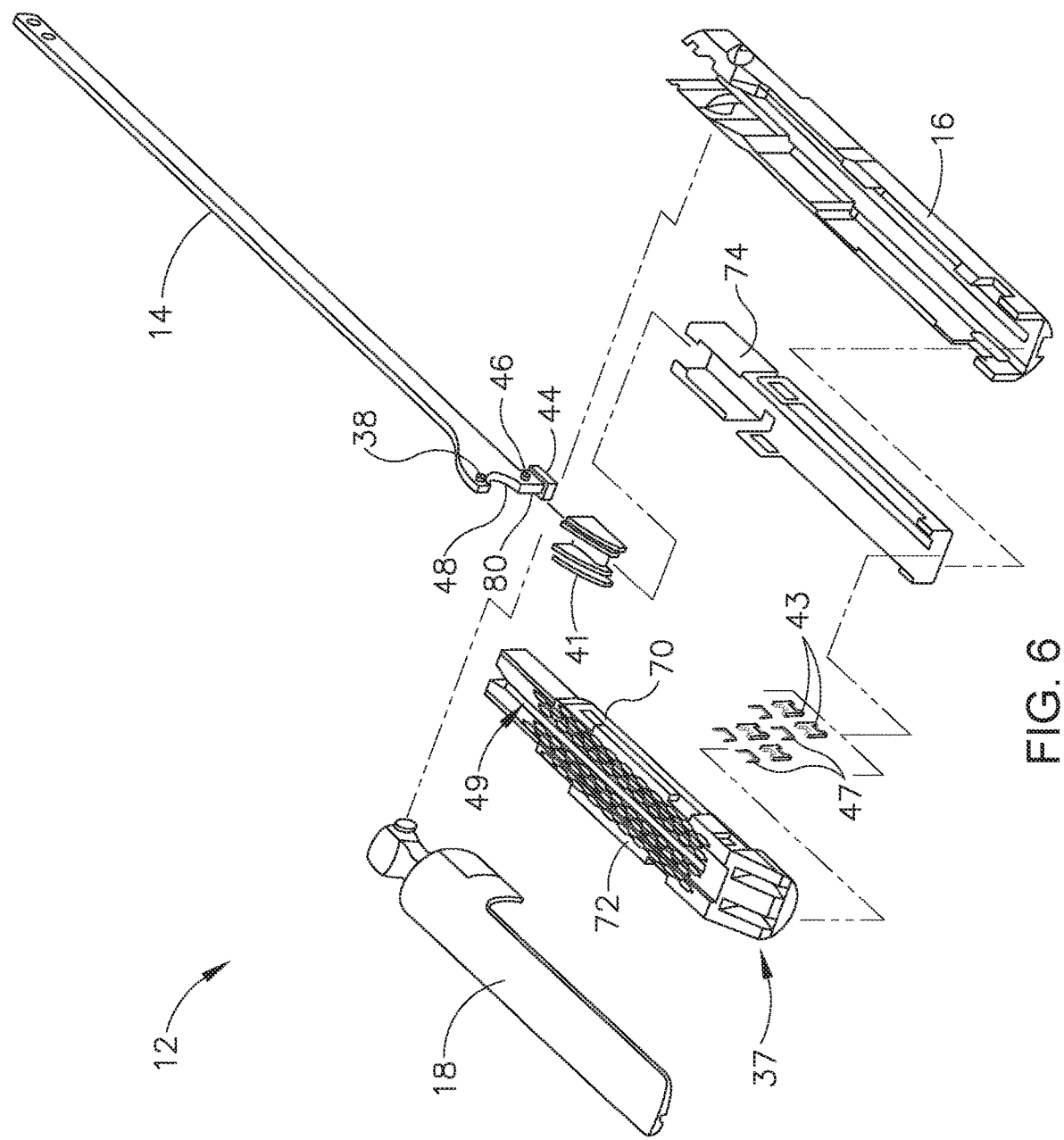
FIG. 6 depicts an exploded perspective view of the end effector of FIG. 3.
Figure 9:
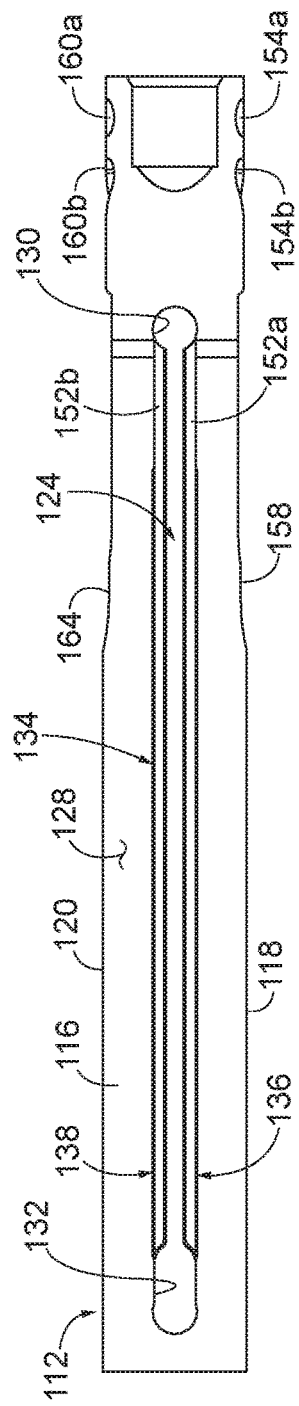
FIG. 9 depicts a bottom view of the lower jaw body of FIG. 7.
Figure 10:
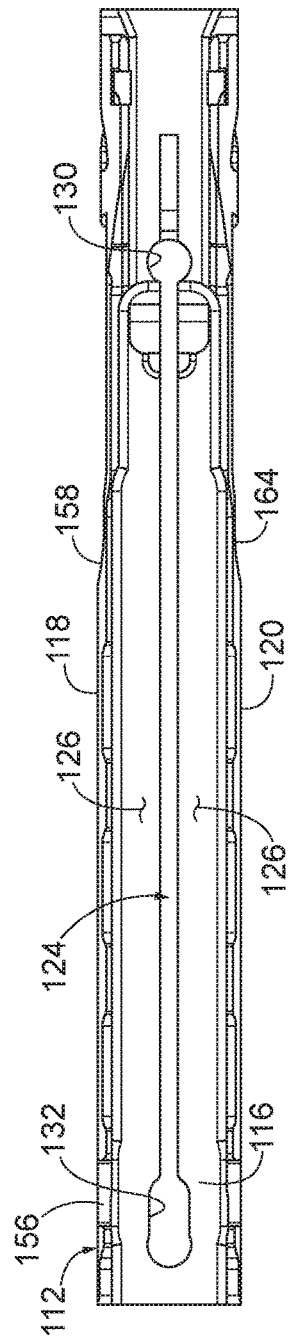
FIG. 10 depicts a top view of the lower jaw body of FIG. 7.
Figure 11:
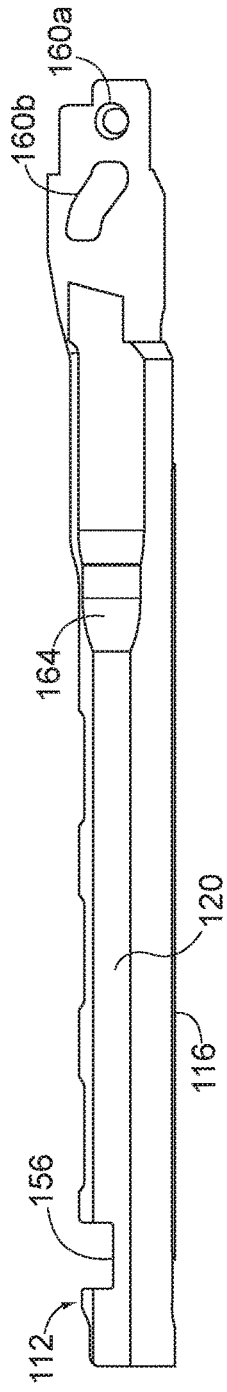
FIG. 11 depicts a left side view of the lower jaw body of FIG. 7.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37). Staple cartridge (37) may be constructed and operable in accordance with at least some of the teachings of U.S. Pat. No. 9,517,065, the disclosure of which is incorporated by reference herein; and/or U.S. Pat. No. 9,808,248, the disclosure of which is incorporated by reference herein.

With end effector (12) closed as depicted in FIGS. 4A-4B by distally advancing closure tube (32) and closure ring (33), firing beam (14) is then advanced in engagement with anvil (18) by having upper pin (38) enter longitudinal channel (42) of anvil (18). A pusher block (80) (shown in FIG. 5) is located at the distal end of firing beam (14) and pushes wedge sled (41) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B; but are shown in FIG. 3. Anvil (18) is intentionally omitted from the view in FIG. 5. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis.

Instrument (10) may otherwise be configured and operable in accordance with any of the teachings of any of the patent references cited herein. Additional exemplary modifications that may be provided for instrument (10) will be described in greater detail below. The below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Lower Jaws, Anvils, and Methods of Manufacture

In some conventional manufacturing processes, lower jaw (16) or anvil (18) of instrument (10) may be machined from a single solid block of material (e.g. metal). As a result, this machining of lower jaw (16) or anvil (18) may be time consuming and expensive, both of which are undesirable. Conventional machining techniques, being reductive in nature, may also be considered as being inefficient since they may create waste in the material that is removed from the single solid block of material. Additionally, in some instances, considerable machining may impart undesirable stresses into lower jaw (16) or anvil (18). As a result, it is desirable to manufacture lower jaw (16) using a faster, more efficient, and more cost-effective process or system of processes to further enhance lower jaw (16) or anvil (18). Additionally, it may be desirable that specific portions and features of lower jaw (16) or anvil (18) have tight tolerances to aid in the use of instrument (10), while other specific portions and features of lower jaw (16) or anvil (18) may have looser tolerances where the precise dimensions are of lesser significance. As such, it is desirable to manufacture an exemplary lower jaw (110, 210) and/or anvil (410, 510) that is efficient, cost effective, and sufficiently robust to interchangeably function with end effector (12) of instrument (10) described above.

As previously indicated, instrument (10) includes a body (shown as handle portion (20)), shaft (22) extending from the body, and end effector (12) in communication with shaft (22). End effector (12) is operable to compress, staple, and cut tissue. End effector (12) may include lower jaw (110, 210) and/or anvil (410, 510) that may be used in place of lower jaw (16) and/or anvil (18) shown in FIG. 1. In other words, and as described in greater detail below, lower jaw (110, 210) may be used in place of lower jaw (16) of instrument (10) and anvil (410, 510) may be used in place of anvil (18) of instrument (10). Additionally, lower jaw (110, 210) may be used with anvil (410, 510). Similar to the operation of instrument (10), where anvil (18) pivots relative to lower jaw (16), anvil (410, 510) pivots relative to lower jaw (110, 210). As such, anvil (410, 510) and lower jaw (210, 310) may clamp tissue similarly to the clamping performed by anvil (18) and lower jaw (16) shown in FIG. 1.

Lower jaw (110, 210) and anvil (410, 510) include a body (e.g. a lower jaw body (112, 212) and an anvil body (412, 512)) and an elongate cap (114, 214, 414, 514, 514a). As will be discussed in greater detail below, elongate cap (114, 214, 414, 514, 514a) is configured to be secured to body (e.g. lower jaw body (112, 212) or anvil body (412, 512)), for example, by welding. Similar to lower jaw (16), lower jaw (110, 210) is also configured to receive a staple cartridge, similar to cartridge (37) shown in FIG. 3. Additional details of lower jaw (110, 210) and anvil (410, 510) are described below with reference to the following figures.

A. First Exemplary Alternative Lower Jaw

FIGS. 7-14A show a first exemplary alternative lower jaw (110). More specifically, FIG. 7 shows a bottom right perspective view of lower jaw (110) as including a lower jaw body (112) coupled with an elongate cap (114), while FIG. 8 shows an exploded bottom right perspective view of lower jaw body (112) separated at a distance from elongate cap (114). Lower jaw body (112) includes a bottom wall (116) interposed between opposing side walls (118, 120) that collectively form an internal cavity (122) configured to receive a staple cartridge (e.g. staple cartridge (37)). Lower jaw body (112) is shown as being generally U-shaped; however, lower jaw body (112) may have a variety of suitable shapes. Bottom wall (116) includes an elongate channel (124) that extends through inner and outer surfaces (126, 128) of bottom wall (116). As shown in FIGS. 7-10, bottom wall (116) extends longitudinally from a proximal aperture (130) to a distal elongated aperture (132). Proximal aperture (130) and distal elongated aperture (132) extend completely through inner and outer surfaces (126, 128) of bottom wall (116).

As shown in FIGS. 7-10 and 12-14A, lower jaw body (112) includes at least one alignment feature (134) disposed in bottom wall (116) adjacent elongate channel (124). Alignment feature (134) is configured to aid in aligning elongate cap (114) with elongate channel (124). Alignment feature (134) may be fixably coupled with elongate cap (114) to at least partially enclose elongate channel (124). For example, aligning feature (134) may aid in aligning and holding elongate cap (114) on lower jaw body (112) before and during when elongate cap (114) is fixably coupled (e.g. welded) with lower jaw body (112). As shown, alignment feature (134) includes first and second recessed portions (136, 138). First and second recessed portions (136, 138) are disposed between outer surface (128) of bottom wall (116) and lower knife track (152a-b). For example, lower knife track (152a-b) may receive firing beam cap (44) shown in FIG. 6 with respect to instrument (10). First and second recessed portions (136, 138) respectively include first and second recessed surfaces (140, 142) separated by elongate channel (124). As shown, first and second recessed surfaces (140, 142) of first and second recessed portions (136, 138) open up to elongate channel (124). As shown in FIG. 12, first and second recessed portions (136, 138) respectively include distal arcuate surfaces (144, 146). Distal arcuate surfaces (144, 146) distally align first and second recessed portions (136, 138) with elongate cap (114). Similarly, as shown in FIG. 13, first and second recessed portions (136, 138) respectively include proximal arcuate surfaces (148, 150). Proximal arcuate surfaces (148, 150) proximally align first and second recessed portions (136, 138) with elongate cap (114).

Side walls (118, 120) extend generally perpendicular to bottom wall (116). Side walls (118, 120) may also include one or more apertures and/or cutouts. As shown in FIGS. 7-11, side wall (118) includes proximal apertures (154a-b), a distal cutout (156), and an inwardly tapering portion (158). Similarly, side wall (120) includes proximal apertures (160a-b), a distal cutout (162), and an inwardly tapering portion (164). Proximal apertures (154a, 160a) are configured to pivotably couple lower jaw (110) with anvil (18).

FIGS. 14-14A show cross-sectional views of lower jaw body (112) and elongate cap (114) of FIG. 7. As shown, elongate cap (114) includes opposing inner and outer surfaces (166, 168). Elongate cap (114) is welded onto lower jaw body (112) to at least partially enclose elongate channel (124). However, elongate cap (114) may be secured to lower jaw body (112) by a variety of different methods and suitable fasteners. Inner surface (166) of elongate cap (114) is fixably coupled (e.g. welded) onto first and second recessed surfaces (140, 142) of first and second recessed portions (136, 138) that are separated by elongate channel (124). As shown, outer surface (168) of elongate cap (114) is configured to extend generally flush with outer surface (128) of bottom wall (116). This minimizes the likelihood of interfering with tissue while end effector (12) is interacting with tissue Elongate cap (114) includes first and second elongate lateral outer sides (172, 174). First and second elongate lateral outer sides (172, 174) are shown as being in contact with first and second elongate lateral outer sides (176, 178) of first and second recessed portions (136, 138).

Lower jaw body (112) and elongate cap (114) may be separately formed using a variety of processes. For example, lower jaw body (112) and elongate cap (114) are each integrally formed as a unitary piece and subsequently coupled together (e.g. welded). Additionally, lower jaw body (112) may be formed using metal injection molding, additive manufacturing, selective laser melting, and/or direct metal laser sintering. Certain manufacturing processes (stamping, additive manufacturing, selective laser melting, direct metal laser sintering, and/or metal injection molding) may result in looser tolerances than desired. Metal injection molding (MIM) refers to any metalworking process where finely-powdered metal is mixed with a binder material to create a feedstock that is subsequently shaped and solidified using molding process (e.g. injection molding). Metal injection molding allows for high volume, complex parts to be shaped.

As shown, lower jaw body (112) is formed using metal injection molding, which may result in about a 5% tolerance with respect the length of lower jaw body (112). Lower jaw body (112) and each of its respective features have a molded shape. Additionally, metal injection molding may leave surface irregularities. In view of the tight tolerances desired for manufacture of instrument (10), it is desirable to refine at least certain specific portions of lower jaw body (112). It may be beneficial to hot isostatic press lower jaw body (112, 212) using a high-pressure vessel. Hot isostatic pressing (HIP) is a manufacturing process that is used to reduce the porosity of metals and increase the density of many ceramic materials. Hot isostatic pressing may result in one or more of densification of powdered components, elimination of internal porosity, improvement of mechanical properties (such as increased resistance to fatigue and temperature extremes, higher resistance to impact, wear and abrasion, and improved ductility), more efficient production (tighter tolerances, reduction in machining, reduction in scrap). Hot isostatic pressing may be used on metal components, ceramic components, and/or composite components. For example, lower jaw body (112) may be placed into high pressure vessel and subjected to high pressurized gases and/or high temperatures. While the hot isostatic pressing likely occurs at a time prior to machining, it is also envisioned that the hot isostatic pressing may occur at a time after machining. It is desirable to selectively use hot isostatic pressing on particular structural features of lower jaw body (112). This refining may be applied to specifically desired features, without refining the entire lower jaw body (112). Additionally, certain features of which may be subsequently machined to a machined shape. Machining certain features may provide many benefits, including improving the dimensional tolerances of the metal injection molding process.

B. Second Exemplary Alternative Lower Jaw

Figure 15:
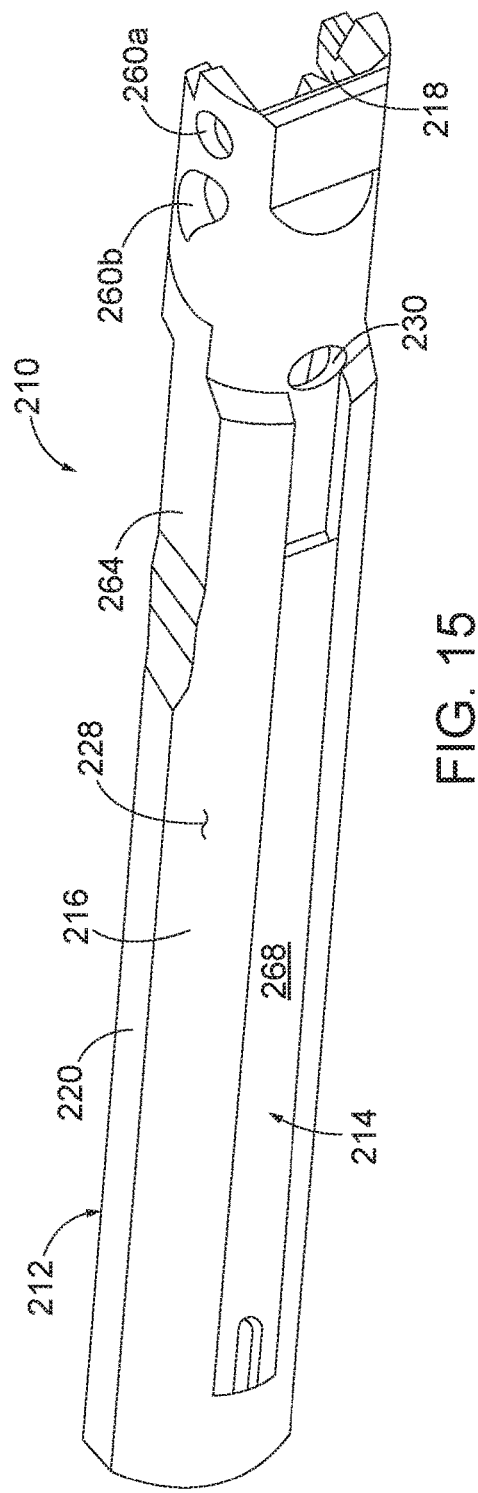
FIG. 15 depicts a left perspective view of a second exemplary alternative lower jaw that may be incorporated into the instrument of FIG. 1.
Figure 16:
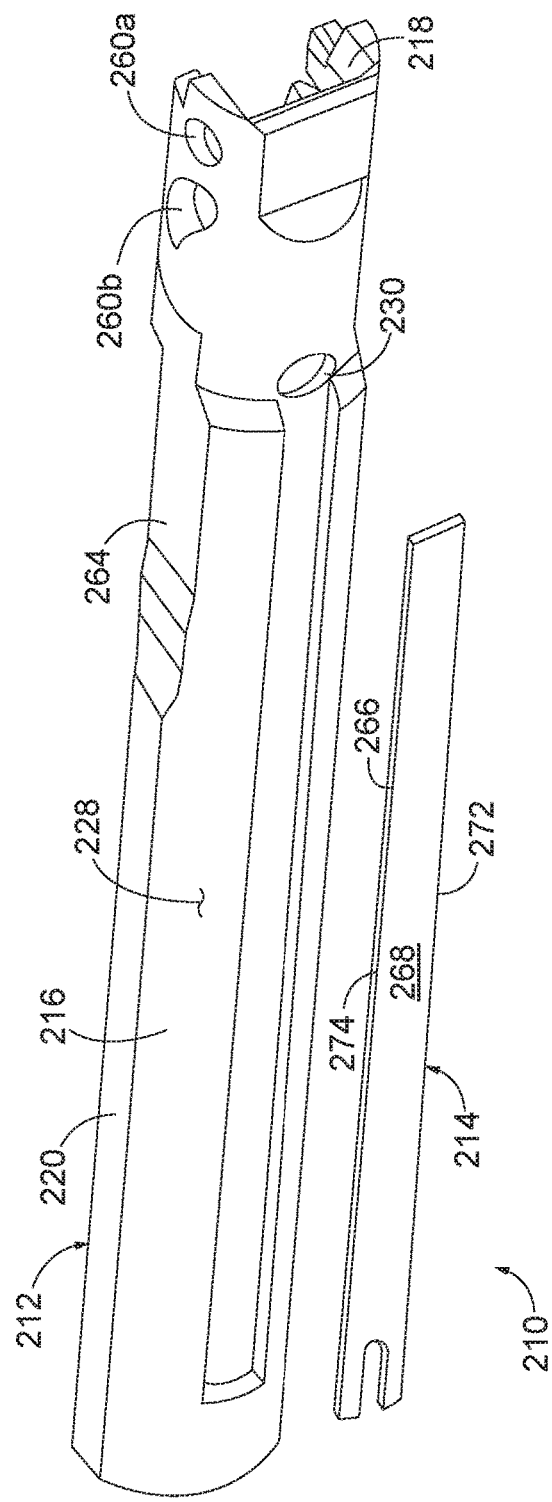
FIG. 16 depicts an exploded left perspective view of the lower jaw of FIG. 15 that includes a lower jaw body separated from an elongate cap.

FIGS. 15 and 16 show a second exemplary alternative lower jaw (210) that is configured to be used in place of lower jaw (16). Similar to lower jaw (110) with similar reference numerals referring similar features, lower jaw (210) includes a lower jaw body (212) and an elongate cap (214). More specifically, FIG. 15 shows a bottom right perspective view of lower jaw (210) as including lower jaw body (212) coupled with elongate cap (214), while FIG. 16 shows an exploded bottom right perspective view of lower jaw body (212) separated at a distance from elongate cap (214). Similar to lower jaw body (112) discussed above with reference to FIGS. 7-14B, lower jaw body (212), includes a bottom wall (216), opposing side walls (218, 220), an internal cavity (222), and an elongate channel (224). Bottom wall (216) is interposed between opposing side walls (218, 220) that collectively form internal cavity (222) that is configured to receive a staple cartridge (e.g. staple cartridge (37)). Similar to bottom wall (116), bottom wall (216) includes an inner surface (226), an outer surface (228), a proximal aperture (230), an alignment feature (234), a first recessed portion (236), a second recessed portion (238), a first recessed surface (240), and a second recessed surface (242).

Unlike lower jaw (110), bottom wall (216) of lower jaw (210) is not shown as including distal elongated aperture (132), distal arcuate surfaces (144, 146), or proximal arcuate surfaces (148, 150). However, one or more of these features may be subsequently machined, similar to the method shown in FIGS. 17A-17C, after lower jaw body (212) is formed. For example, first and second recessed portions (236, 238) may include distal arcuate surfaces (244, 246) similar to distal arcuate surfaces (144, 146) and proximal arcuate surfaces (148, 150) described above with reference to FIGS. 12 and 13. Similar to side wall (120), side wall (220) again includes proximal apertures (260a-b), and an inwardly tapering portion (264). Similar to side wall (118), side wall (218) again includes proximal apertures and an inwardly tapering portion, which are not shown. As shown in FIGS. 15 and 16, lower jaw (210) does not include distal cutouts similar to distal cutouts (156, 162) described above with respect to lower jaw (110). However, if desired, distal cutouts may be imparted similar to distal cutouts (156, 162) of lower jaw (110).

Elongate cap (214) includes an inner surface (266) and an outer surface (268). Similar to elongate cap (114), elongate cap (214) may be manufacturing using a variety of methods (e.g. stamping, injection molding, metal injection molding, additive manufacturing etc.). Elongate cap (214) is configured to provide additional support for bottom wall (216). Outer surface (268) of elongate cap (214) may extend flush with outer surface (228) of bottom wall (216). Elongate cap (214) may be coupled to outer surface (228) of bottom wall (216) before, during, or after machining of lower jaw body (212). For example, elongate cap (214) may be welded to outer surface (228) of bottom wall (216). Elongate cap (214) includes first and second elongate lateral outer sides (272, 274). First and second elongate lateral outer sides (272, 274) of elongate cap (214) may be in contact with first and second elongate lateral outer sides (276, 278) respectively of first and second recessed portions (236, 238), similar to lower jaw body (112) and elongate cap (114) shown in FIG. 14A.

Figure 17A:
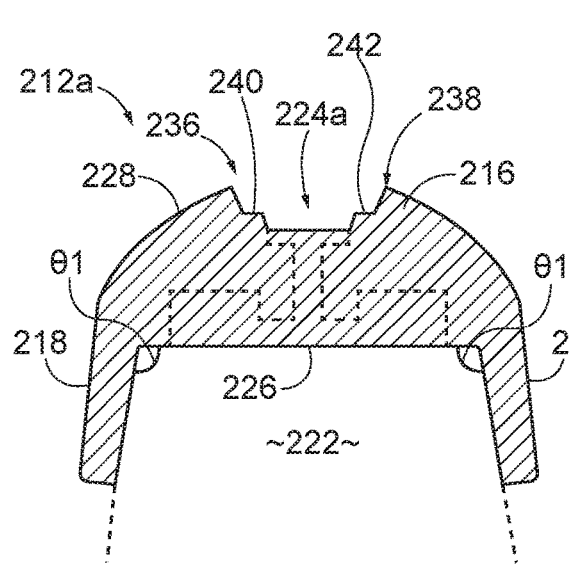
FIG. 17A depicts a schematic sectional view of the lower jaw body of FIG. 16, after being formed but prior to being machined.
Figure 17B:
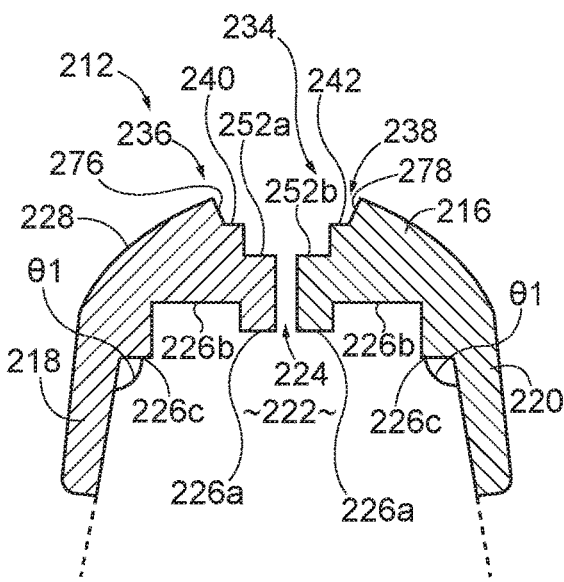
FIG. 17B depicts a schematic sectional view of the lower jaw body of FIG. 17A after being partially machined but prior to being bent.

FIG. 17A shows lower jaw body (212a) similar to FIG. 16, after being formed but prior to being machined. As shown in FIG. 17A-17B, side walls (218, 220) have obtuse interior angles ($\theta 1$) relative to bottom wall (216). More specifically, obtuse interior angle ($\theta 1$) exists between bottom wall (216) and side wall (218), and an obtuse interior angle exists ($\theta 1$) between bottom wall (216) and side wall (220). Obtuse interior angles ($\theta 1$) provide suitable draft angles for a mold (e.g. metal injection molding mold) to be removed. For example, a draft angle of 0.75-1.5 degrees would result in an obtuse angle ($\theta 1$) of approximately 90.75-91.50 degrees. As shown in FIG. 17A, elongate channel (224a) is not formed completely through bottom wall (216). In FIG. 17A, lower jaw body (212a) may have a near net shape defined by the continuous solid line. As used herein, "near net shape" means that the initial forming operations create an intermediate (near net) shape that is very close to the final (net) shape, which reduces the need and associated cost of significant surface finishing. These initial forming operations may include, for example, additive manufacturing, selective laser melting, direct metal laser sintering, and/or metal injection molding. For example, this may be beneficial if tighter tolerances are required for desired operation. The phantom lines in FIG. 17A shows material that is to be removed (e.g. during one or more machining steps).

FIG. 17B shows the lower jaw body (212a) of FIG. 17A after being partially machined but prior to being bent. As shown in FIG. 17B, elongate channel (224) is machined to extend completely through lower jaw body (212). More specifically, elongate channel (224) extends completely through inner and outer surfaces (226a, 228) of bottom wall (216). As shown in FIG. 17B, inner surfaces (226a-c) of lower jaw body (212) include stepped surfaces that are machined into lower jaw body (212) after lower jaw body (212) is formed. Lower knife track (252a-b) is also machined into lower jaw body (212). For example, lower knife track (152a-b) may receive firing beam cap (44) shown in FIG. 6 with respect to instrument (10).

Figure 17C:
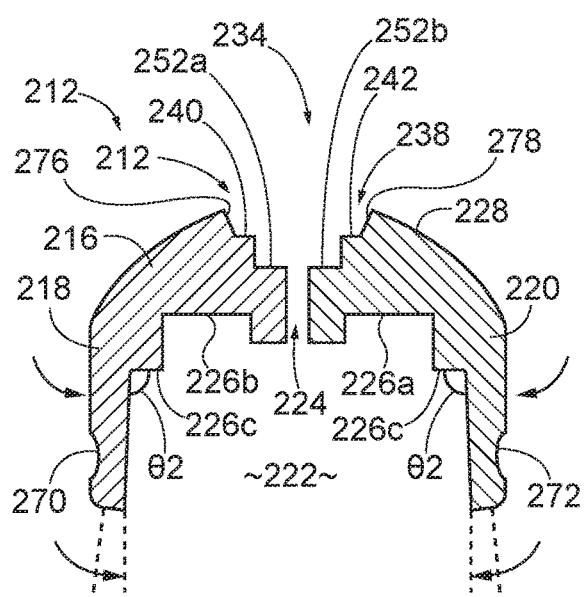
FIG. 17C depicts a schematic sectional view of the lower jaw body of FIG. 17B after being machined and bent.

As shown in FIGS. 17B and 17C, lower jaw body (212) includes at least one alignment feature (234) disposed in bottom wall (216) adjacent elongate channel (224). Alignment feature (234) is configured to aid in aligning elongate cap (214) with elongate channel (224). Alignment feature (234) may be fixably coupled with elongate cap (214) to at least partially enclose elongate channel (224). For example, aligning feature (234) may aid in aligning and holding elongate cap (214) on lower jaw body (212) before and during when elongate cap (214) is fixably coupled (e.g. welded) with lower jaw body (212). As shown, alignment feature (234) includes first and second recessed portions (236, 238). First and second recessed portions (236, 238) are disposed between outer surface (228) of bottom wall (216) and lower knife track (252a-b). First and second recessed portions (236, 238) respectively include first and second recessed surfaces (240, 242) separated by elongate channel (224). As shown, first and second recessed surfaces (240, 242) of first and second recessed portions (236, 238) open up to elongate channel (224) and are generally perpendicular to elongate channel (224).

As shown in FIG. 17C, side walls (218, 220) are bent relative to bottom wall (216) to have approximately 90-degree interior angles ($\theta 2$). More specifically, side wall (218) is bent toward bottom wall (216) and side wall (220) is bent toward bottom wall (216), such that the obtuse angle ($\theta 1$) have approximately 90-degree angles ($\theta 2$). As a result, tissue stops are straight at approximately 0 degrees. Outer notches (270) are also machined into opposing side wall (218, 220).

C. Exemplary Method of Manufacturing a Lower Jaw

Figure 18:
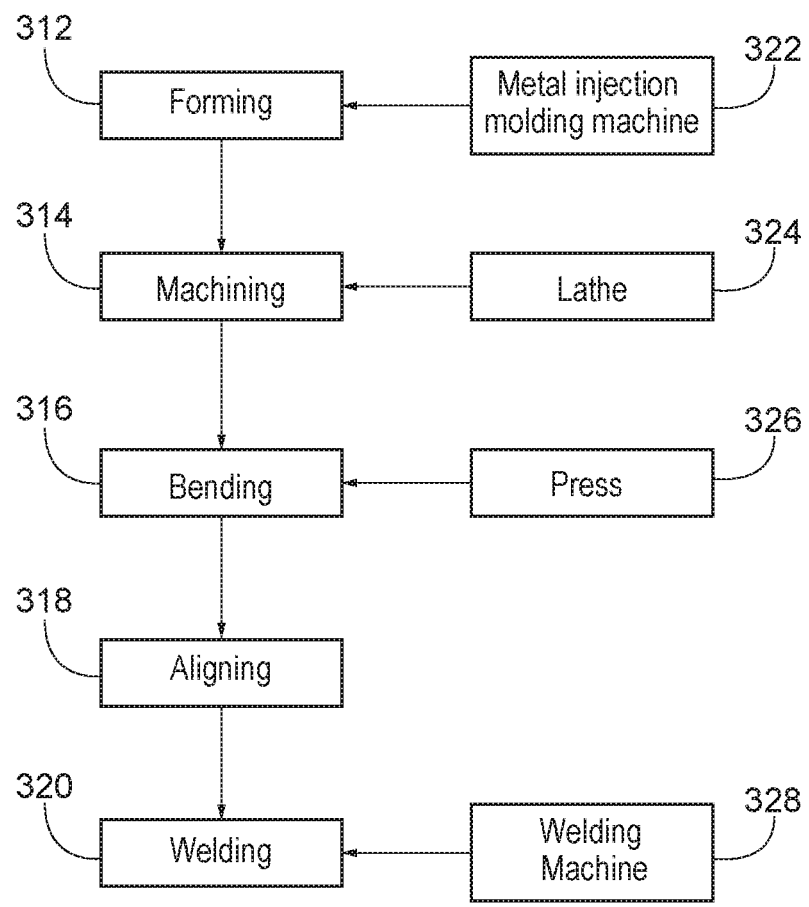
FIG. 18 depicts an exemplary method of manufacturing the lower jaw of FIG. 7.

FIG. 18 shows a method (310) of manufacturing lower jaw (110, 210) of end effector (12) of surgical instrument (10) that includes at least five steps (312, 314, 316, 318, 320). As shown, at step (312), method (310) includes forming lower jaw body (112, 212) using a metal injection molding process such that elongate channel (124, 224) does not extend completely through lower jaw body (112, 212) using a metal injection molding machine (322). As previously discussed, lower jaw body (112, 212) may undergo a hot isostatic pressure process. At step (314), method (310) also includes subsequently machining the elongate channel (124, 224) to extend completely through lower jaw body (112, 212), where elongate channel (124, 224) is configured to receive a portion of a knife therethrough using a lathe (324).

At step (316), method (310) also includes inwardly bending first and second outwardly extending lateral sides (e.g. opposing side walls 118, 120, 218, 220) of lower jaw body (112, 212) to be generally perpendicular with elongate channel (124, 224) using a press (326). At step (318), method (310) also includes aligning elongate cap (114, 214) with elongate channel (124, 224) that extends completely through lower jaw body (112, 212) using at least one alignment feature (134, 234) of lower jaw body (112, 212) that is disposed adjacent elongate channel (124, 224). At step (320), method (310) also includes welding elongate cap (114, 214) onto lower jaw body (112, 212) to at least partially enclose elongate channel (124, 224) using a welding machine (328).

D. First Exemplary Alternative Anvil

Figure 19:
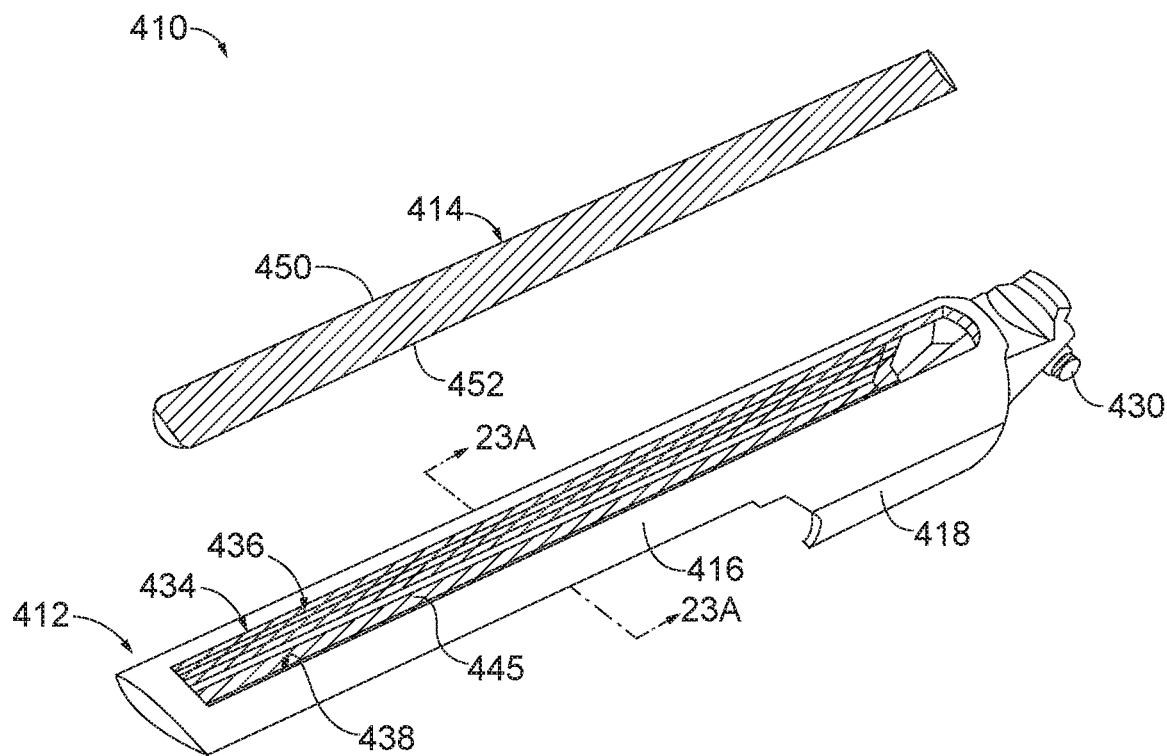
FIG. 19 depicts an exploded top right perspective view of a first exemplary alternative anvil that may be incorporated into the instrument of FIG. 1.
Figure 20:
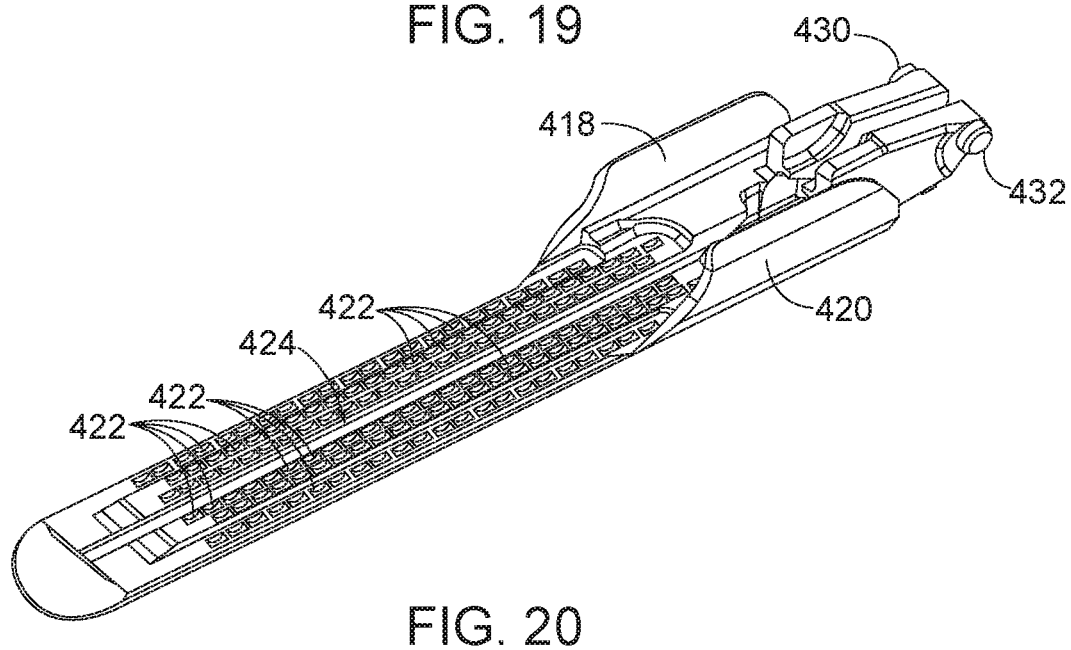
FIG. 20 depicts a bottom left perspective view of an anvil body of the anvil of FIG. 19.

FIGS. 19-29 show a first exemplary alternative anvil (410) that is configured to be used in place of anvil (18) of instrument (10). More specifically, FIG. 19 shows an anvil (410) as including a first exemplary anvil body (412) and a third exemplary elongate cap (414), and FIG. 20 shows a bottom left perspective view of anvil (410). Anvil body (412) includes a top wall (416) interposed between opposing side walls (418, 420). Top wall (416) includes a plurality of staple forming pockets (422) as will be discussed in greater detail with reference to FIGS. 26A-29. Top wall (416) includes an elongate channel (424) that extends through inner and outer surfaces (426, 428) of top wall (416). As shown in FIGS. 19 and 20, anvil body (412) includes first and second pins (430, 432) that are configured to pivotably interact with proximal apertures (160a, 260a) of lower jaw (110, 210).

As shown in FIGS. 19 and 23A-25B, anvil body (412) includes at least one alignment feature (434) disposed in top wall (416) adjacent elongate channel (424). Alignment feature (434) is configured to aid in aligning elongate cap (414) with elongate channel (424). Alignment feature (434) may be fixably coupled with elongate cap (414) to at least partially enclose elongate channel (424). For example, aligning feature (134) may aid in aligning and holding elongate cap (414) on anvil body (412) before and during when elongate cap (414) is fixably coupled (e.g. welded) with anvil body (412). As shown, alignment feature (434) includes first and second recessed portions (436, 438). First and second recessed portions (436, 438) are disposed between outer surface (428) of top wall (416) and upper knife track (444a-b). As shown using hatching in FIG. 19, an inner surface of elongate cap (414) and first and second recessed portions (436, 438) may be machined to improve dimensional tolerances. Upper knife track (444a-b) is configured to receive upper pin (38) shown in FIGS. 3-6 with regard to end effector (12) of instrument (10). FIG. 23A shows anvil body (412a) of FIG. 20 after being formed but prior to being machined to remove machined portion (445) shown in FIGS. 19, 22, and 23A. FIG. 23B shows anvil body (412) of FIG. 23A after being machined. First recessed portion (436) includes a recessed surface (440) that is shown as being generally perpendicular to elongate channel (424) and an outwardly extending lateral inner surface (446) abutting recessed surface (440). Similarly, second recessed portion (438) includes a recessed surface (442) that is shown as being generally perpendicular to elongate channel (424) and an outwardly extending lateral inner surface (448) abutting recessed surface (440). First and second recessed surfaces (440, 442) of first and second recessed portions (436, 438) are separated by elongate channel (424). As shown, first and second recessed surfaces (440, 442) of first and second recessed portions (436, 438) open up to elongate channel (424) and are generally perpendicular to elongate channel (424).

Figure 21:
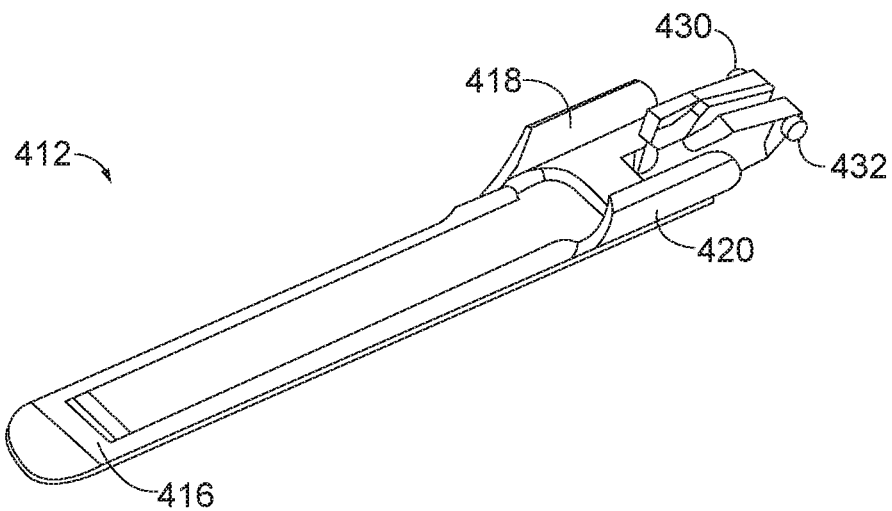
FIG. 21 depicts a bottom left perspective view of the anvil body of FIG. 20, prior to being machined.
Figure 22:
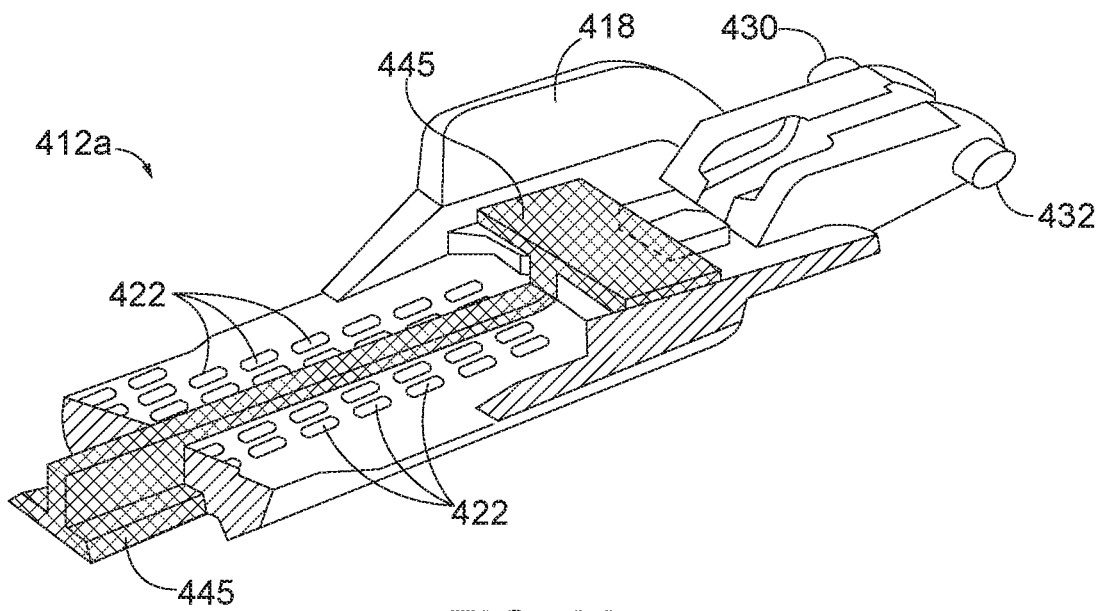
FIG. 22 depicts a schematic sectional bottom left perspective view of FIG. 20, showing a machined portion.

FIG. 21 shows a bottom left perspective view of anvil body (412) of FIG. 19, prior to being machined. While staple forming pockets (422) are not shown as being imparted, staple forming pockets (422) may be imparted when anvil body (412) is formed (e.g. using a metal injection molding process). As shown in FIGS. 19 and 20, first and second pins (430, 432) of anvil body (412) are machined to improve the interaction with proximal apertures (160a, 260a). FIG. 22 shows a sectional bottom left perspective view of FIG. 20, showing machined portion (445) that is configured to be removed using one or more machining processes.

FIG. 24A shows anvil (410A) as including anvil body (412) of FIG. 23B and elongate cap (414) of FIG. 19. FIGS. 24A and 25A collectively show that after welding elongate cap (414) onto anvil body (412), there is a lateral gap (G1) between elongate lateral outer sides (450, 452) of elongate cap (414) and outwardly extending lateral inner surfaces (446, 448) of elongate channel (424) of anvil body (412). For example, lateral gap (G1) may be 0.001-0.003 inches according to one particular embodiment. However, it is envisioned that gap (G1) may vary. As shown in FIGS. 24A-25B, elongate cap (414) includes first and second elongate lateral outer sides (450, 452) and opposing inner and outer surfaces (456, 458). Elongate cap (414) is welded onto lower jaw body (412) to at least partially enclose elongate channel (424). At least a portion of inner surface (456) of elongate cap (414) is fixably coupled (e.g. welded) onto first and second recessed surfaces (440, 442) of first and second recessed portions (436, 438) that are separated by elongate channel (424). Elongate cap (414) may be welded onto lower jaw body (412) by welding first elongate lateral outer side (450) with outwardly extending lateral inner surface (446) and by welding second elongate lateral outer side (452) with outwardly extending lateral inner surface (448). As shown, outer surface (458) of elongate cap (414) is configured to extend generally flush outer surface (428) of bottom wall (416). However, one or more welds may protrude from gap (G1).

As shown in FIGS. 24B and 25B, elongate cap (414a) includes a notch (454) adjacent an inner surface (456a) that includes planar surfaces (460). More specifically, FIG. 24B shows anvil body (412a) of FIG. 23B and an elongate cap (414a). FIG. 25B shows an enlarged portion of the fit between anvil body (412a) and elongate cap (414a) of FIG. 24B. As shown, outer surface (458a) of elongate cap (414a) does not include a notch. Outer surface (458a) is generally flush with outer surface (428) of top wall (416). However, a variety of notches (454) are envisioned including arcuate surfaces and V-shaped surfaces are also envisioned. Elongate cap (414a) may be bent along notch (454) to reduce lateral gap (G1) as compared to elongate cap (414) shown in FIGS. 24A and 25A. For example, lateral gap (G2) in FIG. 25B is less than 0.001 inches. Elongate cap (414a) may be welded onto lower jaw body (412) by welding first elongate lateral outer side (450a) with outwardly extending lateral inner surface (446) and by welding second elongate lateral outer side (452a) with outwardly extending lateral inner surface (448). As shown, outer surface (458a) of elongate cap (414a) is configured to extend generally flush outer surface (428) of bottom wall (416). However, one or more welds may protrude from gap (G2).

As shown, anvil body (412) and elongate cap (414, 414a) are each integrally formed as a unitary piece and subsequently coupled together. For example, anvil body (412) and elongate cap (414) may be separately formed using a variety of processes including metal injection molding. Metal injection molding (MIM) refers to any metalworking process where finely-powdered metal is mixed with a binder material to create a feedstock that is subsequently shaped and solidified using molding process (such as injection molding). Metal injection molding allows for high volume, complex parts to be shaped. Anvil body (412) and each of their respective features have a molded shape.

Certain features of which may be subsequently machined to a machined shape. Machining certain features may provide many benefits, including improving the dimensional tolerances of the metal injection molding process. However, it is envisioned that if desired, two or more of these components may be integrally formed together as a unitary piece. However, anvil body (412) may be formed using a variety of processes including additive manufacturing, selective laser melting, direct metal laser sintering, and/or metal injection molding. Certain manufacturing processes (stamping, additive manufacturing, selective laser melting, direct metal laser sintering, and/or metal injection molding) may result in looser tolerances than desired. In view of the tight tolerances desired for manufacture of instrument (10), it is desirable to refine at least certain specific portions of anvil body (412) to improve the dimensional accuracy of anvil body (412).

Staple forming pockets (422) may be formed simultaneously with or after anvil body (412) is formed. For example, FIG. 21 shows a perspective views of anvil body (412), but with staple forming pockets (422) not yet formed. As described in greater detail with reference to FIG. 20, at least a portion of anvil body (412) may be machined after forming anvil body (412) if desired.

Figure 26A:
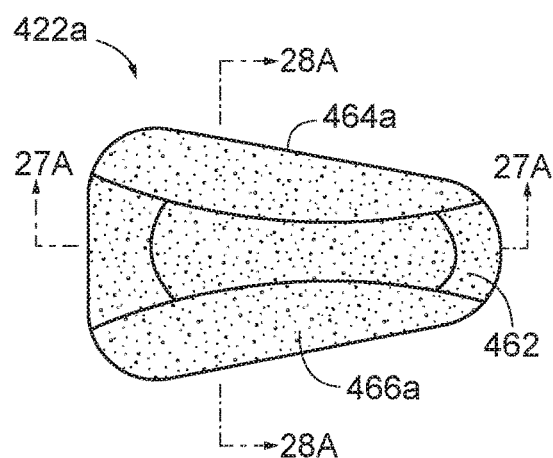
FIG. 26A depicts a staple forming pocket of FIG. 20 prior to being coined or electrochemically machined.

As shown in FIGS. 26A-29, at least a portion of staple forming pocket (422) may be coined or electrochemical machined after forming staple forming pocket (422) using an injection molding process (e.g. a metal injection molding process). More specifically, FIG. 26A shows a staple forming pocket (422a) prior to being coined or electrochemically machined, while FIG. 26B shows staple forming pocket (422) of FIG. 26A, after being coined or electrochemically machined. As shown in FIG. 26A, staple forming pocket (422a) includes a central portion (462a) disposed between outer portions (464a, 466a). As shown in FIGS. 26B, 27B, and 28B, central portion (462) of staple forming pocket (422) is subsequently coined or electrochemically machined, which results in a smoother surface and a denser surface than another portion (e.g. outer portions (464, 466)) that was not coined or electrochemical machined. As a result, outer portions (464, 466) have surface that is rougher and less dense than central portion (462) of staple forming pocket (422). In other words, non-machined portions (e.g. outer portions (464a, 466a)) of staple forming pocket (422) have a first surface finish and machined portions (e.g., central portion (462)) of staple forming pocket (422) have a second surface finish, where the second surface finish is finer than the first surface finish. Alternatively, the entire staple forming pocket (422), including outer portions (464, 466), may be coined or electrochemically machined, if desired.

Coining is a form of precision stamping where a workpiece is subjected to a sufficiently high stress to induce plastic flow on the surface of the material. The plastic flow reduces surface grain size and work hardens the surface of the workpiece, while the material deeper within the workpiece retains its toughness and ductility. Coining also improves the dimensional tolerances of staple forming pocket (422). Electrochemical machining (ECM) is a method of removing metal using one or more electrochemical processes. Electrochemical machining may be used for mass production due to cost effectiveness and is utilized for working extremely hard materials or materials that are difficult to machine using conventional methods. Electrochemical machining may cut small or uniquely-shaped angles, intricate contours, or cavities in hard metals workpieces.

Figure 26B:
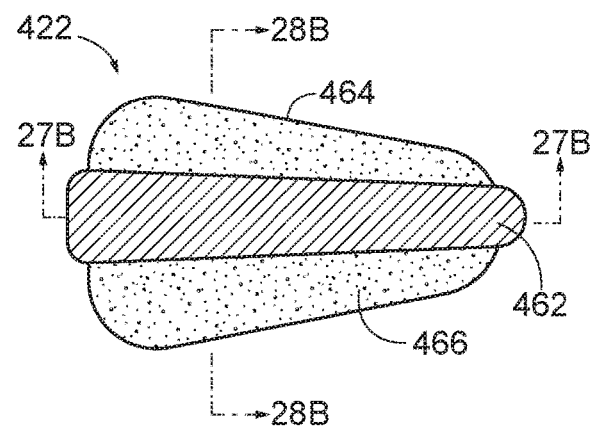
FIG. 26B depicts the staple forming pocket of FIG. 20, but after being coined or electrochemically machined.
Figure 27A:
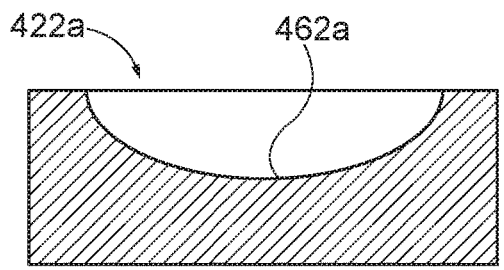
FIG. 27A depicts a schematic sectional view of a central portion of the staple forming pocket of FIG. 26A, taken along line 27A-27A of FIG. 26A.
Figure 27B:
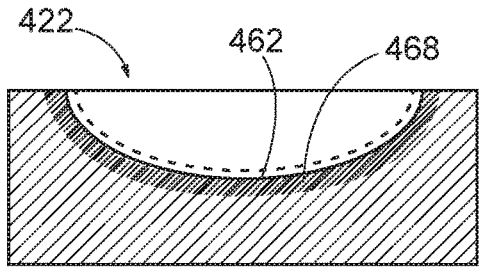
FIG. 27B depicts a schematic sectional view of a central portion of the staple forming pocket of FIG. 26B, taken along line 27B-27B of FIG. 26B.

FIG. 27A shows central portion (462a) of staple forming pocket (422a) taken along line 27A-27A of FIG. 26A, while FIG. 27B shows central portion (462) of staple forming pocket (422), taken along line 27B-27B of FIG. 26B. As shown when comparing FIG. 27A with FIG. 27B, central portion (462a) having been coined or electrochemically machined is both smoother and denser than another portion (e.g. outer portions (464, 466)) of the same staple forming pocket (422) that was not coined or electrochemically machined.

Figure 28A:
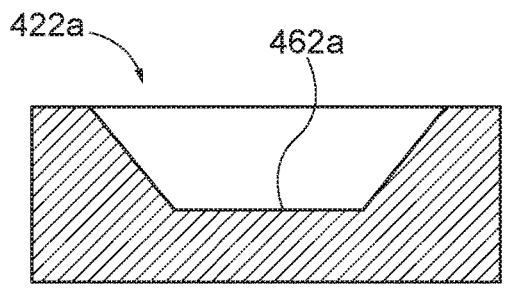
FIG. 28A depicts a schematic sectional view of a portion of the staple forming pocket of FIG. 26A, taken along line 28A-28A of FIG. 26A.
Figure 28B:
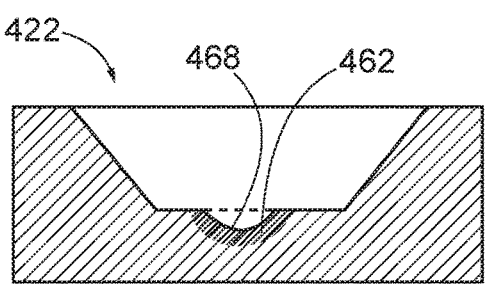
FIG. 28B depicts a schematic sectional view of a portion of the staple forming pocket of FIG. 26B, taken along line 28B-28B of FIG. 26B.
Figure 29:
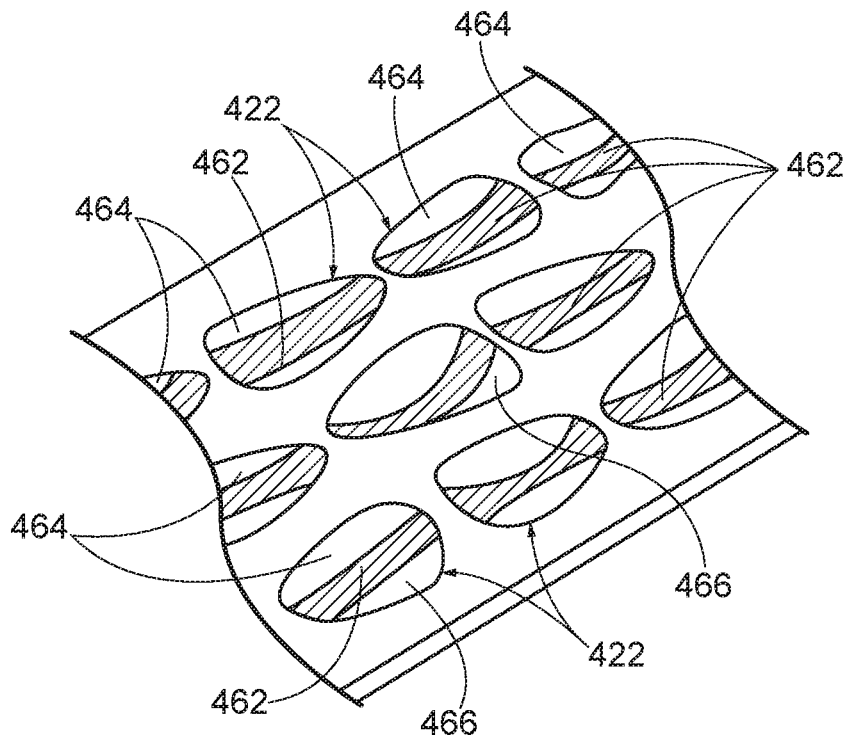
FIG. 29 depicts a plurality of individual staple forming pockets of FIG. 26B after being coined or electrochemically machined.

FIG. 28A shows a portion of staple forming pocket (422a) of FIG. 26A, taken along line 28A-28A, while FIG. 28B shows a portion of staple forming pocket (422) of FIG. 26B, taken along line 28B-28B. As shown when comparing FIG. 28A with FIG. 28B, a channel (468) results after the coining or electrochemical machining process. FIG. 29 shows a plurality of staple forming pockets (422) of FIG. 26B, after being coined or electrochemically machined. More specifically, central portions (462) are coined or electrochemically machined.

D. Second Exemplary Alternative Anvil

Figure 30:
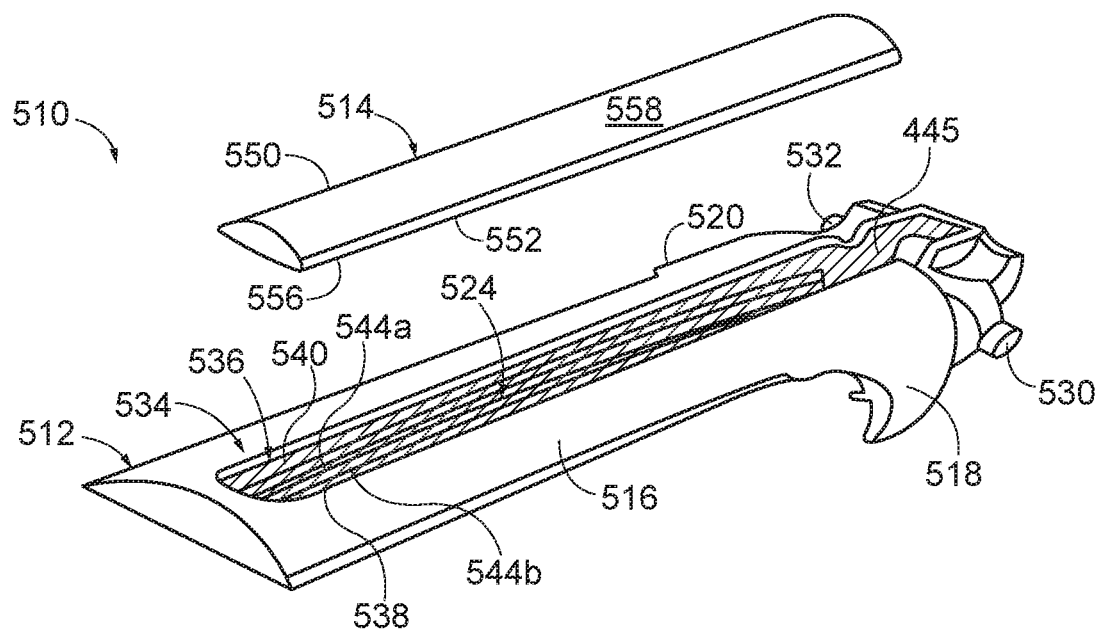
FIG. 30 depicts an exploded top right perspective view of a second exemplary alternative anvil that may be incorporated into the instrument of FIG. 1.

FIG. 30 show a second exemplary alternative anvil (510) that is configured to be used in place of anvil (18). Similar to anvil (410) with similar reference numerals referring similar features, anvil (510) includes an anvil body (512)

and an elongate cap (514). Similar to anvil body (412), anvil body (512) includes a top wall (516), opposing side walls (518, 520), an elongate channel (524), inner surface (not shown), an outer surface (528), a first pin (530), a second pin (532), at least one alignment feature (534), a first recessed portion (536), a second recessed portion (538), a recessed surface (540), upper knife track (544a), and a machined portion (545). Upper knife track (544a) is configured to receive upper pin (38) shown in FIGS. 3-6 with regard to end effector (12) of instrument (10). Similar to elongate cap (414), elongate cap (514) includes first and second elongate lateral outer sides (550, 552) and opposing inner and outer surface (556, 558). Machined portion (545) may be removed after anvil body (512) is formed using one or more machining processes. Similar to staple forming pockets (422), anvil (510) also includes a plurality of staple forming pockets that are not shown.

E. Exemplary Method of Manufacturing an Anvil

Figure 31:
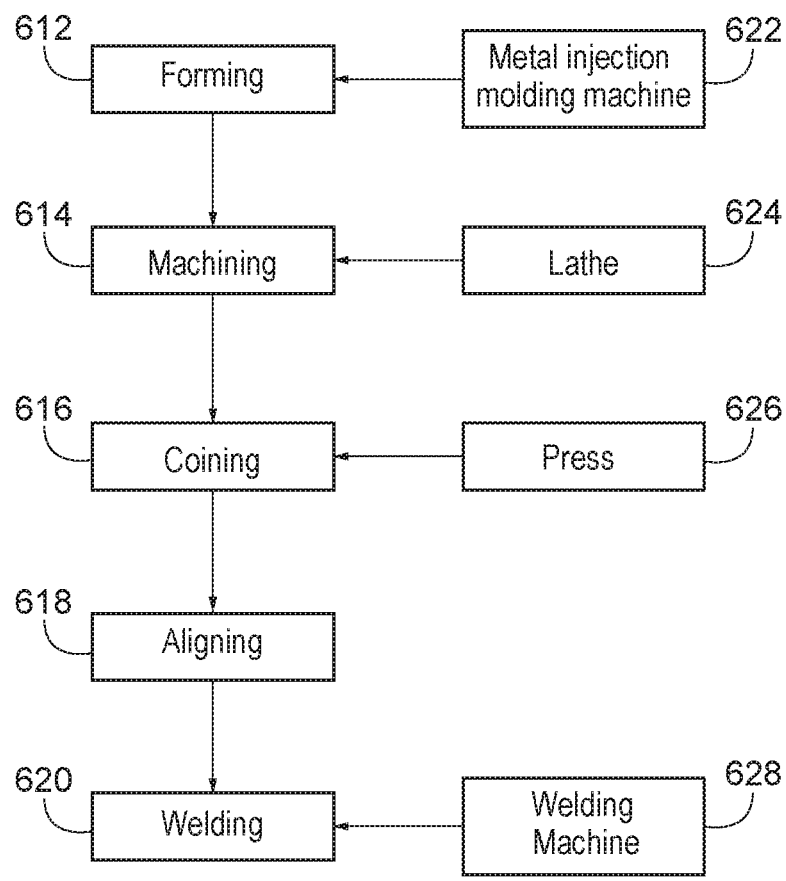
FIG. 31 depicts an exemplary method of manufacturing the anvil of FIG. 19.

FIG. 31 shows a method (610) of manufacturing anvil (410, 510) of end effector (12) of surgical instrument (10) that includes at least five steps (612, 614, 616, 618, 620). At step (612), method (610) includes forming anvil body (412, 512) using a metal injection molding process such that elongate channel (424, 524) does not extend completely through anvil body (412, 512). Step (612) may be performed, for example, using a metal injection molding machine (622). However, it is also envisioned that anvil body (412, 512) may be formed using additive manufacturing.

At step (614), method (610) includes subsequently machining elongate channel (424, 524) to extend completely through anvil body (412, 512), where elongate channel (424, 524) is configured to receive a portion of a knife (e.g. upper pin (38)) therethrough. For example, upper knife track (444a-b, 544a) is configured to receive upper pin (38) shown in FIGS. 3-6 with regard to end effector (12) of instrument (10). It is envisioned that the machining of elongate channel (424, 524) may happen before, simultaneously with, or after coining of staple forming pockets (422, 522). Step (612) may be performed using a variety of machining tools, for example, using a lathe (624), which may be manually operated or automated. The exemplary method (610) using near net shapes reduce the need for costly machining by providing anvil (410, 510) already having one or more features already imparted.

At step (616), method (610) includes coining or electrochemical machining at least a portion of at least one staple forming pocket 422, 522) using a press (626). At step (618), method (610) includes aligning elongate cap (414, 514) with elongate channel (424, 524) that extends completely through anvil body (412, 512) using at least one alignment feature of anvil body (412, 512) that is disposed adjacent elongate channel (424, 524). At step (620), method (610) includes welding elongate cap (414, 514) onto anvil body (412, 512) to at least partially enclose elongate channel (424, 524) using a welding machine (628).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of manufacturing an end effector of a surgical instrument, wherein the end effector includes first and second opposing jaws, wherein the first jaw includes a body and an elongate cap, the method comprising: (a) providing the elongate cap and the body of the first jaw of the end effector, wherein the body includes an elongate channel and at least one alignment feature; (b) aligning the elongate cap with the elongate channel that extends completely through the body using the at least one alignment feature of the body that is disposed adjacent the elongate channel; and (c) welding the elongate cap onto the body to at least partially enclose the elongate channel.

Example 2

The method of Example 1, wherein welding the elongate cap onto the body further comprises welding an interior surface of the elongate cap onto an exterior surface of the alignment feature.

Example 3

The method of Example 1, wherein the alignment feature comprises at least one recessed portion that includes a recessed surface, wherein welding the elongate cap onto the body further comprises welding an interior surface of the elongate cap onto the recessed surface of the alignment feature.

Example 4

The method o of Example 1, wherein the alignment feature comprises first and second recessed portions, wherein the first and second recessed portions respectively include first and second recessed surfaces separated by the elongate channel, wherein welding the elongate cap onto the body further comprises welding an interior surface of the elongate cap onto the first and second recessed surfaces that are separated by the elongate channel.

Example 5

The method of Example 4, wherein the first and second recessed portions comprise proximal and distal arcuate surfaces, wherein aligning the elongate cap with the elongate channel further comprises proximally and distally aligning the elongate cap by using the proximal and distal arcuate surfaces.

Example 6

The method of any one or more of Examples 1 through 5, wherein providing the body further comprises forming the body using a metal injection molding process such that the elongate channel does not extend completely through the body; and subsequently machining the elongate channel to extend completely through the body.

Example 7

The method of any one or more of Examples 1 through 6, wherein the body comprises an anvil body or a lower jaw body, wherein the method further comprises machining a portion of a knife track into the anvil body or the lower jaw body.

Example 8

The method of any one or more of Examples 1 through 7, wherein after welding the elongate cap onto the body there is an elongate gap between lateral outer sides of the elongate cap and lateral inner surfaces of the elongate channel of the body.

Example 9

The method of Example 8, wherein the elongate cap includes a notch, wherein the method further comprises bending the elongate cap along the notch to reduce the elongate gap.

Example 10

The method of any one or more of Examples 1 through 9, wherein the body includes at least one of an anvil body or a lower jaw body, wherein providing the elongate cap and the body of the first jaw further comprises metal injection molding at least one of an anvil body or a lower jaw body.

Example 11

The method of any one or more of Examples 1 through 10, wherein the at least one alignment feature of the body aligns the elongate cap with the elongate channel both before and during welding.

Example 12

The method of any one or more of Examples 1 through 11, further comprising: inwardly bending first and second outwardly extending lateral sides of the lower jaw body to be generally perpendicular with the elongate channel.

Example 13

The method of any one or more of Examples 1 through 5 and Examples 8 through 9, wherein the body comprises an anvil body, wherein the method further comprises metal injection molding a plurality of staple forming pockets of the anvil body.

Example 14

The method of Example 13, wherein after metal injection molding the plurality of staple forming pockets, the method further comprises coining or electrochemical machining at least a portion of at least one staple forming pocket of the plurality of staple forming pockets, wherein the portion coined or electrochemically machined is both smoother and denser than another portion that was not coined or electrochemical machined.

Example 15

The method of Example 14, wherein the portion coined or electrochemically machined is a central portion of at least one staple forming pocket of the plurality of staple forming pockets.

Example 16

A method of manufacturing an end effector of a surgical instrument, wherein the end effector includes first and second opposing jaws, wherein the first jaw includes a body and an elongate cap, wherein the body includes an elongate channel, the method comprising: (a) forming the body using a metal injection molding process such that the elongate channel does not extend completely through the body; (b) subsequently machining an elongate channel to extend completely through the body, wherein the elongate channel is configured to receive a portion of a knife therethrough; and (c) welding the elongate cap onto the body to at least partially enclose the elongate channel.

Example 17

The method of Example 16, further comprising: machining an inner surface of the elongate cap prior to welding the elongate cap onto the body.

Example 18

An instrument, comprising: (a) a handle portion; (b) a shaft extending from the handle portion; and (c) an end effector in communication with the shaft, wherein the end effector is operable to compress, staple, and cut tissue, wherein the end effector includes a lower jaw and an anvil, wherein at least one of the lower jaw or the anvil comprises: (i) an elongate cap that includes first and second opposing surfaces, and (ii) a body that includes: (A) an elongate channel extending completely therethrough the body, and (B) at least one alignment feature disposed adjacent the elongate channel, wherein the alignment feature is fixably coupled with the first surface of the elongate cap to at least partially enclose the elongate channel.

Example 19

The instrument of Example 18, wherein the alignment feature comprises at least one recessed portion that includes a recessed surface, wherein the first surface of the elongate cap is fixably coupled with the recessed surface of the alignment feature.

Example 20

The instrument of Example 18, wherein the alignment feature comprises first and second recessed portions, wherein the first and second recessed portions respectively include first and second recessed surfaces separated by the elongate channel, wherein the first surface of the elongate cap is fixably coupled onto the first and second recessed surfaces that are separated by the elongate channel.

Example 21

The instrument of Example 18, wherein the alignment feature is fixably coupled with the first surface of the elongate cap to at least partially enclose the elongate channel.

Example 22

The instrument of any one or more of Examples 18 through 21, wherein an interior surface of the elongate cap is welded onto an exterior surface of the alignment feature.

Example 23

The instrument of Example 18, wherein the alignment feature includes at least one recessed portion, wherein the at least one recessed portion includes a recessed surface, wherein an interior surface of the elongate cap is welded onto the recessed surface of the alignment feature.

Example 24

The instrument of Example 18, wherein the alignment feature comprises first and second recessed portions, wherein the first and second recessed portions respectively include first and second recessed surfaces separated by the elongate channel, wherein an interior surface of the elongate cap is welded onto the first and second recessed surfaces that are separated by the elongate channel.

Example 25

The instrument of any one or more of Examples 20 and 24, wherein the first and second recessed portions comprise proximal and distal arcuate surfaces, wherein the elongate cap is configured to be proximally and distally aligned using the proximal and distal arcuate surfaces.

Example 26

The instrument of any one or more of Examples 18 through 25, wherein the body is formed using a metal injection molding process such that the elongate channel does not extend completely through the body, wherein the elongate channel is subsequently machined to extend completely through the body.

Example 27

The instrument of any one or more of Examples 18 through 26, wherein the body comprises an anvil body or a lower jaw body, wherein a portion of a knife track is machined into the anvil body or the lower jaw body.

Example 28

The instrument of any one or more of Examples 18 through 27, wherein an elongate gap extends between lateral outer sides of the elongate cap and lateral inner surfaces of the elongate channel of the body.

Example 29

The instrument of any one or more of Examples 18 through 28, wherein the elongate cap includes a notch, wherein the elongate cap is configured to be bent along the notch to reduce the gap.

Example 30

The instrument of any one or more of Examples 18 through 26 and Examples 28 through 29, wherein the body includes at least one of an anvil body or a lower jaw body, wherein at least one of an anvil body or a lower jaw body is formed using metal injection molding.

Example 31

The instrument of any one or more of Examples 18 through 30, wherein the at least one alignment feature of the body is configured to align the elongate cap with the elongate channel both before and during welding.

Example 32

The instrument of any one or more of Examples 18 through 31, wherein first and second outwardly extending lateral sides of the body are configured to be bent inwardly to be generally perpendicular with the elongate channel.

Example 33

The instrument of any one or more of Examples 18 through 26 and Examples 28 through 29, wherein the body comprises an anvil body, wherein a plurality of staple forming pockets are formed into the anvil body using metal injection molding.

Example 34

The instrument of Example 33, wherein at least a portion of at least one staple forming pocket of the plurality of staple forming pockets is coined or electrochemical machined such that the portion coined or electrochemically machined is both smoother and denser than another portion that was not coined or electrochemical machined.

Example 35

The instrument of Example 34, wherein the portion coined or electrochemically machined is a central portion of at least one staple forming pocket of the plurality of staple forming pockets.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of manufacturing an end effector of a surgical instrument, wherein the end effector includes first and second opposing jaws, wherein the first jaw includes a body and an elongate cap, the method comprising:
    (a) providing the elongate cap and the body of the first jaw of the end effector, wherein the body includes an elongate channel and at least one alignment feature;
    (b) aligning the elongate cap with the elongate channel that extends completely through the body using the at least one alignment feature of the body that is disposed adjacent the elongate channel; and
    (c) welding the elongate cap onto the body to at least partially enclose the elongate channel.

2. The method of claim 1, wherein welding the elongate cap onto the body further comprises welding an interior surface of the elongate cap onto an exterior surface of the alignment feature.

3. The method of claim 1, wherein the alignment feature comprises at least one recessed portion that includes a recessed surface, wherein welding the elongate cap onto the body further comprises welding an interior surface of the elongate cap onto the recessed surface of the alignment feature.

4. The method of claim 1, wherein the alignment feature comprises first and second recessed portions, wherein the first and second recessed portions respectively include first and second recessed surfaces separated by the elongate channel, wherein welding the elongate cap onto the body further comprises welding an interior surface of the elongate cap onto the first and second recessed surfaces that are separated by the elongate channel.

5. The method of claim 4, wherein the first and second recessed portions comprise proximal and distal arcuate surfaces, wherein aligning the elongate cap with the elongate channel further comprises proximally and distally aligning the elongate cap by using the proximal and distal arcuate surfaces.

6. The method of claim 1, wherein providing the body further comprises forming the body using a metal injection molding process such that the elongate channel does not extend completely through the body; and subsequently machining the elongate channel to extend completely through the body.

7. The method of claim 1, wherein the body comprises an anvil body or a lower jaw body, wherein the method further comprises machining a portion of a knife track into the anvil body or the lower jaw body.

8. The method of claim 1, wherein after welding the elongate cap onto the body there is an elongate gap between lateral outer sides of the elongate cap and lateral inner surfaces of the elongate channel of the body.

9. The method of claim 8, wherein the elongate cap includes a notch, wherein the method further comprises bending the elongate cap along the notch to reduce the elongate gap.

10. The method of claim 1, wherein the body includes at least one of an anvil body or a lower jaw body, wherein providing the elongate cap and the body of the first jaw further comprises metal injection molding at least one of an anvil body or a lower jaw body.

11. The method of claim 1, wherein the at least one alignment feature of the body aligns the elongate cap with the elongate channel both before and during welding.

12. The method of claim 11, further comprising:
    inwardly bending first and second outwardly extending lateral sides of the lower jaw body to be generally perpendicular with the elongate channel.

13. The method of claim 1, wherein the body comprises an anvil body, wherein the method further comprises metal injection molding a plurality of staple forming pockets of the anvil body.

14. The method of claim 13, wherein after metal injection molding the plurality of staple forming pockets, the method further comprises coining or electrochemical machining at least a portion of at least one staple forming pocket of the plurality of staple forming pockets, wherein the portion coined or electrochemically machined is both smoother and denser than another portion that was not coined or electrochemical machined.

15. The method of claim 14, wherein the portion coined or electrochemically machined is a central portion of at least one staple forming pocket of the plurality of staple forming pockets.

16. A method of manufacturing an end effector of a surgical instrument, wherein the end effector includes first and second opposing jaws, wherein the first jaw includes a body and an elongate cap, wherein the body includes an elongate channel, the method comprising:
  (a) forming the body using a metal injection molding process such that the elongate channel does not extend completely through the body;
  (b) subsequently machining an elongate channel to extend completely through the body, wherein the elongate channel is configured to receive a portion of a knife therethrough; and
  (c) welding the elongate cap onto the body to at least partially enclose the elongate channel.

17. The method of claim 16, further comprising:
machining an inner surface of the elongate cap prior to welding the elongate cap onto the body.

\* \* \* \* \*